United States Patent [19]
Yamamoto et al.

[11] Patent Number: 6,156,506
[45] Date of Patent: *Dec. 5, 2000

[54] METHOD FOR DETECTING A TARGET SUBSTANCE IN A SAMPLE, UTILIZING PYRYLIUM COMPOUND

[75] Inventors: Nobuko Yamamoto, Isehara; Tadashi Okamoto, Yokohama, both of Japan

[73] Assignee: Canon Kabushiki Kaisha, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/825,586

[22] Filed: Apr. 1, 1997

Related U.S. Application Data

[63] Continuation of application No. 08/450,688, May 25, 1995, abandoned.

[30] Foreign Application Priority Data

| May 26, 1994 | [JP] | Japan | 6-112626 |
| Jun. 7, 1994 | [JP] | Japan | 6-125040 |

[51] Int. Cl.$^7$ ................................ C12Q 1/68
[52] U.S. Cl. .................................... 435/6
[58] Field of Search .............................. 435/6

[56] References Cited

U.S. PATENT DOCUMENTS

| 3,786,369 | 1/1974 | Drexhage et al. | 531/945 |
| 4,341,894 | 7/1982 | Regan et al. | 544/333 |
| 4,555,396 | 11/1985 | Frank et al. | 424/3 |
| 4,840,784 | 6/1989 | Frank et al. | 424/3 |
| 5,229,297 | 7/1993 | Schnipelsky et al. | 436/94 |
| 5,278,043 | 1/1994 | Bannworth et al. | 536/23.1 |
| 5,324,829 | 6/1994 | Bahl et al. | 536/23.1 |
| 5,591,578 | 1/1997 | Meade et al. | 435/6 |

FOREIGN PATENT DOCUMENTS

| 0229943 | 7/1987 | European Pat. Off. | |
| 0232967 | 8/1987 | European Pat. Off. | |
| 320308 | 12/1988 | European Pat. Off. | C12Q 1/68 |
| 0315491 | 5/1989 | European Pat. Off. | |
| 455517 | 7/1991 | European Pat. Off. | C12Q 1/68 |
| 487218 | 10/1991 | European Pat. Off. | C12Q 1/68 |
| 0512334 | 11/1992 | European Pat. Off. | |
| 599337 | 6/1994 | European Pat. Off. | C12Q 1/68 |
| 2-75958 | 3/1980 | Japan . | |
| 59-133460 | 7/1984 | Japan . | |
| 63-238166 | 10/1988 | Japan . | |
| 1-153683 | 6/1989 | Japan . | |
| 2-295496 | 12/1990 | Japan . | |
| WO 86-06374 | 11/1986 | WIPO . | |
| WO89-10415 | 11/1989 | WIPO . | |
| 93-10267 | 5/1993 | WIPO . | |
| 0643140 | 3/1995 | WIPO . | |
| 95-15971 | 6/1995 | WIPO . | |

OTHER PUBLICATIONS

"A DNA Probe of Ruthenium bipyridine Complex Using Photocatalytic Activity", Chemistry Letters, pp. 1889–1892 (1989), Kojima et al.
J.Am.Chem.Soc. 1989, 111, pp. 7721–7726, Telser et al.
J.Am.Chem.Soc. 1989, 111, pp. 7226–7232, Telser et al.
J.Am.Chem.Soc. 1990, 112, pp. 4960–4962, Friedman et al.
J.Am.Chem.Soc. 1992, 114, pp. 8736–8738, Jenkins et al.
"Photoelectro Transfer Between Molecules Adsorbed in Restricted Spaces", Photochem. Convers, etc., Turro N. et al., 1990, pp. 123–139.
J. Photochem. Photobiol. 1988, 47, 85S, Helene C. et al.
Nucleic Acids Res. 1987, 15, 8643–8659, T.L. Doan et al.
J.Am.Chem. Soc.1993, 115, pp. 2508–2510, Riesser, et al.
C. Picard et al., "Detection and Enumeration of Bacteria in Soil by Direct DNA Extraction and Polymerase Chain Reaction", *Appl. and Env. Microbio.* 58, 9, 2717–22 (1992).
O. Strobel et al., "Preparation and Characterization of Spin–Labeled Oligonucleotides for DNA Hybridization", *Bioconjugate Chem.*, 1991, 2 89–95 (1991).
P. Cullis et al., "Electron Conduction and Trapping in DNA—An Electron Spin Resonance Study", *J. Chem. Soc.—Faraday Trans.*, 86(3), 591–92 (1990).
Barton, JACS, vol. 108, pp. 6391–6393 (1986).
M. Puruggnan et al., "Accelerated Electron Transfer Between Metal Complexes Mediated by DNA", *Science*, 241, Sep. 23, 1988, 1645–49.
Fromherz, et al. "Photoinduced . . . methylviologen", JACS, vol. 108, pp. 5361–5362 (1986).
Ulicky, et al., Comp. Dict. of Phys Chem. p. 103 (1992).
Detty, et al., "Chalcogenapyrylium . . . Oxidase", J. Med. Chem. vol. 33, pp. 1108–1116, (1990).
Balaban et al., "Regioselective . . . Groups", J. Labelled Cmpds and Radiopharm., vol. 19, No. 6, pp. 783–793 (1982).
Detty, "Rational . . . dyes", New Directions in Photodynamic Therapy, vol. 847, pp. 68–73 (1987).
Yamamoto, et al., "Novel . . . DNA," Nucleic Acids Sym. Series, No. 29, pp. 83–84 (1993).
Sanford, et al., "The Growth . . . Cells", J. Nat'l. Cancer Inst., vol. 9, No. 3, pp. 229–246 (1948).
Haucke, et al. "Absorbtion . . . Salts", Ber. Bunsonques. Phy. Chem. vol. 96, No. 7, pp. 880–886 (1992).

(List continued on next page.)

*Primary Examiner*—Mary E. Ceperley
*Attorney, Agent, or Firm*—Fitzpatrick, Cella, Harper & Scinto

[57] ABSTRACT

A method for detecting a target substance in a sample comprises the steps of providing at least two reagents which can form a reaction system for causing changes as the result of an interaction therebetween the interaction being caused only when the target substance is present in the sample, reacting the reagents with the target substance, and measuring the resulting changes based on the interaction, wherein at least one of the reagents forming the reaction system is selected from specific pyrylium compounds.

67 Claims, 3 Drawing Sheets

OTHER PUBLICATIONS

Shimidzu, et al., "Synthesis . . . properties", 19th Symp. on Nuc. Acids. Chem, pp. 97–98 (1992).

Wizinger, et al. Helv. Chim. Acta., vol. 39, No. 2, Fas. I, p. 5–15 (1956).

Newer Methods of Prep. Org. Chem., vol. II, Acad. Press pp. ix–xiv (1963).

Brun, et al. "Dynamics . . . Bases", J. Am. Chem. Soc., vol. 114, p. 3656–3660 (1992).

Cardullo, et al. "Detection . . . transfer", Proc. Natl. Acad. vol. 85, p. 8790–94 (1988).

Rahman, et al. "Complexes . . . Cu (II)", Carcinogenesis, vol. II, No. 11, p. 2001–3 (1990).

Balaban, et al., "Charge–Transfer . . . Iodides", Tetrahedron, vol. 20, pp. 119–130 (1963).

Morrison, et al, "Solution . . . Hybridization", Anal. Biochem, vol. 183, pp. 231–244 (1989).

Basting, et al. "New Laser Dyes", Appl. Phys., vol. 3, pp. 81–88 (1974).

Latt, et al. "New . . . Acids", Cytometry, vol. 5, No. 4, pp. 339–347 (1984).

Murphy, et al. "Long–Range . . . Helix", Science, vol. 262, pp. 1025–1029 (1993).

Smits, et al. "Relationship . . . Dimethylsulfoxide", Anal. Chem. vol. 45, No. 2, pp. 339–342 (1973).

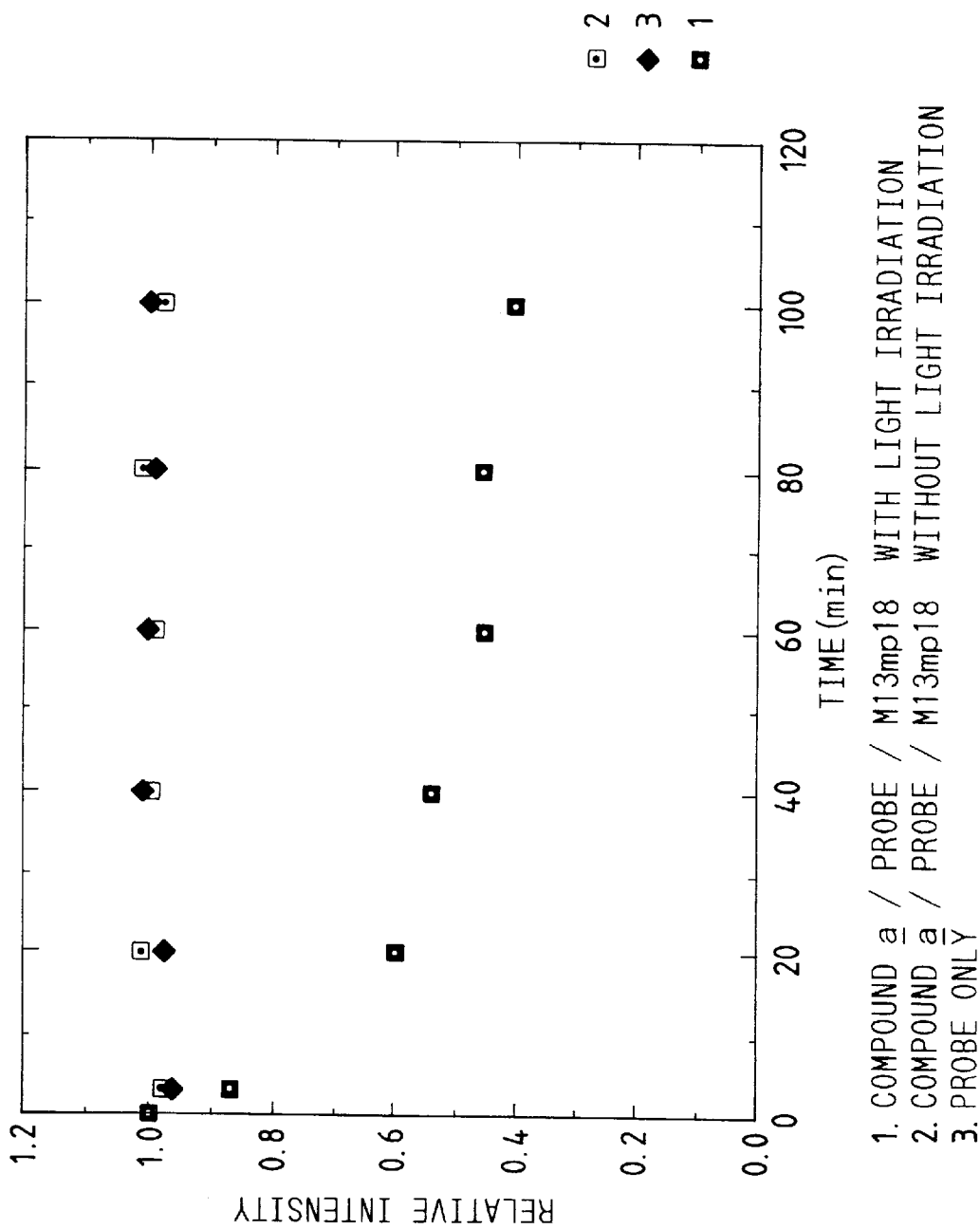

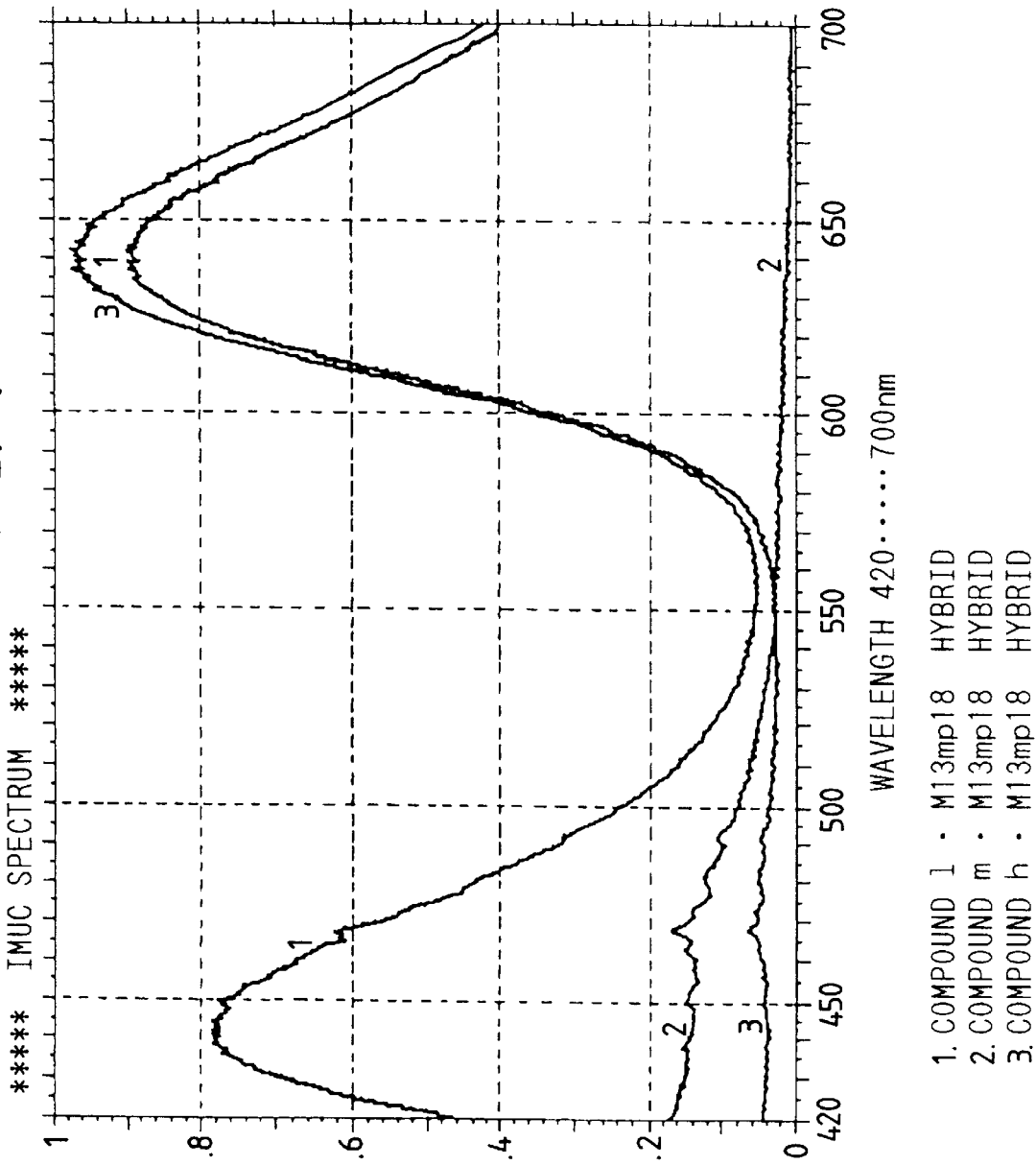

METHOD FOR DETECTING A TARGET SUBSTANCE IN A SAMPLE, UTILIZING PYRYLIUM COMPOUND

This application is a continuation of application Ser. No. 08/450,688 filed May 25, 1995, now abandoned.

BACKGROUND OF THE INVENTION

1. Field of the Invention

This invention relates to a method for detecting a target substance by utilizing plural reagents which can form a reaction system causing a change based on an interaction mediating the target substance, for example, a method useful for detection and identification of a desired base sequence of nucleic acids (DNA or RNA) of virus, microbes, animals, plants, and human beings, and detection of mutation in base sequences, and detection of various substances with immune reactions such as immunoassay.

2. Related Background Art

With advances of analytical techniques of nucleic acids, various kinds of mutation genes have been found, and hereditary diseases caused by gene mutations have been gradually clarified. Gene mutations include partial base deletion and base point mutation, which have been found to cause protein mutation, resulting in various kinds of symptoms. Presently, the hereditary diseases were mainly determined by assays utilizing enzymes or immunological methods utilizing antibodies after symptoms appeared. However, it is said that detection of mutant gene is important at an early stage before severe symptoms appear.

DNA diagnosis is applicable not only for detection of genes of human beings, but for identification of infecting bacteria.

Conventionally, bacterial strain has been identified based on the analogy of morphological and biochemical properties in separated bacteria. This method has the following disadvantages; it requires much time for culture; the same properties can be differently judged by utilizing different methodologies; and different results are obtained for identification when some properties are more predominantly considered than other ones in analysis.

Recent years, DNA-DNA hybridization method and DNA-RNA hybridization method have been tried to detect and identify pathogenic bacteria in bacterial infections. The methods comprise the following steps; extraction of nucleic acids (DNA or RNA) from bacteria, selection of specific part of nucleic acids from bacteria, detection of a base sequence of high homology with the base sequence of the specific part in test nucleic acid samples according to hybridization, and judgement of the subjective bacteria in the samples.

A new method for detecting a specific base sequence of nucleic acid, PCR method, is also utilized. This method comprises the following steps; selection of a specific sequence in a target nucleic acid, preparation of primers required for amplification of the specific sequence, conduction of PCR utilizing the target nucleic acid as a template, detection of the amplified specific sequence, and detection of the target nucleic acid. Use of PCR method improves sensitivity for in detection of nucleic acids. Hybridization is therefore replaced with PCR for detection of nucleic acids in various kinds of fields.

However, PCR method can detect a specific sequence only when a subjective specific base sequence is apparent and an optimal primer is amplified. Primer often combines with a target nucleic acid in non-specific manner, and such sequences as essentially not to be amplified are often formed. Although abnormal gene such as deletion in a target nucleic acid can be determined by analyzing the length of the nucleic acid, abnormal genes such as point mutation which does not change the nucleic acid in length can be determined by no means.

Hybridization is not completely replaced with PCR, but it is also utilized as a method for easily detecting gene.

In hybridization, a probe DNA and a target DNA are combined through a hydrogen bond at their sequence parts which are complementary with each other, in order to form a hybrid. Since a probe cannot be combined with a nucleic acid having a complementary sequence at higher temperatures, and a probe inversely combines with a nucleic acid in non-specific manner in lower temperatures, optimal reaction temperature and ionic strength need to be selected in order to accurately form between the complementary sequences. Further, to make hybridization more accurate, such probes as combining in non-specific manner or mismatching need to be washed by reducing the salt concentration of the hybridization solution or by elevating the temperature of the solution. Therefore, many trials and errors are needed to determine adequate conditions for reaction and washing.

For gene diagnosis, conditions for hybrid forming reaction and washing should be determined more precisely to exclude even a mismatch of one base pair.

Conventionally, hybridization reaction was conducted by immobilizing target nucleic acids on a carrier such as nitrocellulose. The hybridization requires many complicated manipulations, and a novel technique such as hybridization in a solution is expected to develop to make manipulations easy. In the hybridization with no immobilization of nucleic acid immobilization, the largest problem is how to discriminate the objective probes combined with target nucleic acids from excessive probes which are not combined (B/F separation). Moreover, it is important to determine adequate conditions for reaction and washing so that non-specific absorption or mismatch of probes may be excluded for this hybridization as well as for the conventional hybridization utilizing immobilized nucleic acids.

Several methods utilizing fluorescence depolarization are provided in order to detect hybrid of target nucleic acid and probe no B/F separation (Japanese Patent Appln. Laid-Open Nos. 2-295496 and 2-75958). In these methods, a fluorescent-labelled single stranded DNA probe is contacted with DNA in a sample to form a double stranded DNA, fluorescence polarizations before and after the formation of the double stranded DNA are measured, and the resulting variation is evaluated in order to determine whether a base sequence corresponding to the probe base sequence resides in the sample DNA or not. This method is based on the principle that fluorescent substance combined with the single stranded probe get hard to move in the formation of the double stranded DNA, resulting in elevated fluorescence anisotropy.

Although the methods need not B/F separation, they have the following defects: contaminants such as protein in a sample can adsorb to the probe DNA in non-specific manner to increase background for hybrid detection; complicated manipulations are therefore required to exclude the contaminants in advance, non-specifically absorbed probe DNA and pseudo-hybrid due to base mismatch should be excluded in advance when different solution system is utilized, and the concentration of the probe DNA should be almost the same as that of the target DNA to precisely measure the variation of fluorescence.

Gardullo et al. provide three methods for detection of hybrid utilizing energy transfer (Proc. Nalt. Acad. Sci. USA, 85, 8790–8794). All of the methods utilize fluorescein and acridine orange as an energy donor, and rhodamine as an energy acceptor, and conduct the following hybridizations; (i) hybridization of oligonucleotide labelled with fluorescein at its 5' terminal and its complementary oligonucleotide labelled with rhodamine at its 5' terminal, (ii) hybridization of oligonucleotide labelled with fluorescein at its 5' terminal and its complementary DNA, and (iii) hybridization of oligonucleotide labelled with rhodamine and its complementary DNA in the presence of acridine orange. The hybridizations are phenomena that excited energy of the donor is transferred to the neighboring acceptor when excited light and fluorescence in the neighboring fluorescence chromophore are overlapped, leading to shortened lifespan of the donor, quenching of the donor fluorescence, elevated fluorescence strength, etc. The methods are epochal in that hybridization can be detected in a solution and a series of complicated manipulations for immobilization are omitted. However, their sensitivities are lower in several orders compared to the conventional hybridizations. Therefore, modification of the fluorescence chromophore and drastic progress of a detection system have been expected for practical use.

Recently, it is reported that double stranded DNA are mixed with dyes of two kinds in free condition and charge transfer is detected through DNA between the dyes (J. Ame. Chem. Sco., 1992, 114, 3656–3660). In the study, an electron donor having fluorescence (ethidium bromide or acridine orange) is irradiated with lights of wavelengths corresponding to the respective excited wavelengths, and the fluorescence light strength is then reduced in the presence of another dye (an electron acceptor: N,N-dimethyl-2,7-diazapyrenium dichloride). It is considered that both of the dyes are intercalator, and the electron is transferred from the electron donor through DNA double helix to the electron acceptor. However, the degree of the transfer is too low to detect hybrid. Also, the dyes have fluorescence even in free condition, and background of the dye fluorescence should be always considered, even when the variation of the fluorescence strength is detected.

As described above, complicated manipulations are needed to prevent or exclude non-specific adsorption of probes and mismatch of combination, not only for the conventional hybridization utilizing immobilization of target nucleic acids but for the methods such as fluorescence depolarization which require no B/F separation. Moreover, optimal conditions for the manipulations are varied according to the length of a probe and a base sequence for use, and the conditions need to be evaluated and determined for each case. Specifically, the conditions for hybridization need to be determined for each case by considering the possible mismatch based on the fact that the base position of mismatched probe can be an important factor affecting the stability of hybrid, and some mismatched hybrids cannot be excluded dependently on the mismatched position.

The detection systems in a solution utilizing charge transfer or energy transfer are easier for manipulation than the conventional methods which require immobilization of target nucleic acids and B/F separation. However, they are not practically applicable because of low sensitivity. Since the conventionally used dyes have fluorescence even in free condition, it is difficult to decide that the variation of the detected fluorescence strength is caused by an interaction of the energy donor and the energy acceptor (i.e. the electron donor and the electron acceptor) through DNA, by a simple quenching of the solution, or by effects of contaminants.

SUMMARY OF THE INVENTION

In order to overcome the above-mentioned problems caused by the conventional techniques, a method for detection of target nucleic acids is provided which does not require B/F separation for detection of hybrid, comprises simple steps, and provides high sensitivity. An object of the invention is to further provide an appropriate method to accurately detect the desired hybrid only even when mismatched hybrid is present.

An object of the invention is also to provide a useful system for detecting various kinds of substances utilizing immunological reactions such as immunoassay.

An object of the invention is further to provide a method of detecting target nucleic acids by accurately detecting the desired hybrid only even when mismatched hybrid is present.

A method for detecting a target substance in a sample comprising the steps of: providing at least two reagents which can form a reaction system for causing changes as the result of an interaction therebetween, the interaction being caused only when the target substance is present in the sample, reacting the reagents with the target substance; and measuring the resulting changes based on the interaction, wherein at least one of the reagents forming the reaction system is selected from pyrylium compounds of the following formula [I]:

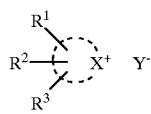

[I]

In the formula [I],

is a heterocyclic ring, and X is O, S, Se, or Te.

$R^1$ and $R^2$ are independently hydrogen atom, halogen atom, sulphonate group, amino group, styryl group, nitro group, hydroxy group, carboxy group, cyano group, substituted or non-substituted lower alkyl group, substituted or non-substituted aryl group, substituted or non-substituted lower alkyl group, or substituted or non-substituted cycloalkyl group, $R^3$ is —A or —L—A, L is —$L^1$—, —$L^2$—$L^3$—, or —$L^4$—$L^5$—$L^6$—, and $L^1$ to $L^6$ are independently —(CH=CH)—, divalent group derived from substituted or non-substituted aryl group, substituted or on-substituted lower alkylene group, or —CH=$R^4$— ($R^4$ is cyclic ring having oxo group), A is substituted or non-substituted aryl group, or —CH=$R^5$ ($R^5$ is substituted or non-substituted heterocyclic ring, substituted or non-substituted cycloalkyl group, or substituted or non-substituted aromatic ring).

Hydrogen atom which is combined with carbon atom not combined with $R^1$, $R^2$, or $R^3$ in pyrylium ring or its analogous ring containing X may be substituted with halogen atom, sulphonate group, amino group, styryl group, nitro group, hydroxyl group, carboxyl group, cyano group, substituted or non-substituted lower alkyl group, substituted or non-substituted aryl group, or substituted or non-substituted lower aralkyl group, and $Y^-$ is anion.

A method for detecting a nucleic acid double helix structure comprising the steps of: providing at least two reagents which can form a reaction system for causing changes as the result of an interaction therebetween, the interaction being caused only when the nucleic acid double helix structure is present in the sample, reacting the reagents with the double helix structure; and measuring the resulting changes based on the interaction wherein at least one of the reagents forming the reaction system is selected from pyrylium compounds of the formula [I].

A method for detection of immunological reaction by reacting a substance for detection with a primary reactant and a secondary reactant in this order both of which cause immunological reaction, and by detecting a formation of a composite, wherein each of the primary and secondary reactants are labelled with at least two reagents which can form a reaction system for causing changes based on an interaction therebetween through a composite obtained from a reaction of the reactants, and at least one of the reagents forming the reaction system is pyrylium compounds of the formula [I].

A method for detecting of nucleic acid hybrid including a double helix structure, which is formed by reacting a nucleic acid probe with a target nucleic acid in a sample solution comprising the steps of:

providing at least two reagents including a first reagent and a second reagent, the first reagent being bound to the probe and the second reagent being contained in the sample solution, the reagents being capable of interacting each other through the double helix structure of the hybrid;

adding the nucleic acid probe combined with the first reagent into the sample solution containing the target nuleic acid and the second reagent to form a double helix structure between the nucleic acid probe and the target nucleic acid; and detecting a change of the reagent, wherein at least one of the reagent is a pyrylium compound represented by the formula [I].

A method for detecting a nucleic acid hybrid including a double helix structure, which is formed by reacting a nucleic acid probe with a target nucleic acid in a sample solution comprising the steps of:

providing a nucleic acid probe combined with a reagent which can interact with the double helix structure of the hybrid to cause a change of nucleic acid of the double helix structure or the reagent;

adding the nucleic acid probe into the sample solution containing the target nucleic acid to form the double helix structure; and detecting a change of nucleic acid or the reagent, wherein said reagent is a pyrylium compound represented by the formula [I].

A probe for detection of a target nucleic acid, which has a sequence for hybridizing with the target nucleic acid, characterized in that;

the probe is combined with at least one of reagents for causing detectable changes based on an interaction through a double helix structure formed by hybridization with the target nucleic acid, and the reagents include at least one of pyrylium system compounds of the formula [I].

A probe for detection of a target nucleic acid, which has a sequence for hybridizing with the target nucleic acid, characterized in that the probe is combined with a pyrylium compound of the formula [I] for causing detectable changes through an interaction with a double helix structure formed with hybridization with the target nucleic acid.

BRIEF DESCRIPTION OF THE DRAWINGS

FIG. 3 shows ESR spectrum of [4] in Example 5.

FIG. 4 shows fluorescence spectrum of [5] in Example 8.

DETAILED DESCRIPTION OF THE PREFERRED EMBODIMENTS

An interaction according to the invention is caused by two substances through a reaction system containing a target substance. Examples of the interaction include give-and-take of charge (electron transfer) and energy (energy transfer). For charge transfer, one of the two substances for causing the interaction is an electron donor, and another is an electron acceptor. For energy transfer, one is an energy donor, and another is an energy acceptor. According to the invention, reagent groups containing two kinds of substances are utilized to cause an interaction in the presence of a target substance, and the resulting variation is measured for detection of the target substance. Specific pyrylium compounds or pyrylium analogous compounds (hereinafter referred to pyrylium compounds) are utilized for at least one of the reagents for causing the interaction.

The reaction system according to the invention can be applicable for detection of immunological reaction by causing the interaction between reagents when a hybride is formed by reaction of a first reacting substance and a second reactive substance for a subject substance for detection in immunological reactions such as immunoassay. For example, in an immunoassay, one of the first and the second reacting substance is labelled with a reagent such as an energy donor or an electron donor, and another is labelled with a reagent such as an acceptor (e.g. an energy acceptor and an electron acceptor) which is complementary to the donor, the reacting substances are immunologically reacted, i.e., the first and the second reacting substances were combined with each other so that the neighboring donor and acceptor causes energy and charge transfer to generate detectable signals, and immunological reaction can be detected. For at least one of the reagents for labelling, specific pyrylium compounds can be utilized.

The present invention will now be described by utilizing a typical example for detecting nucleic acid double helix as a target substance. It is noted that the present invention should not be restricted thereto, as far as the nucleic acid is detected by a similar mechanism.

Figure 1:
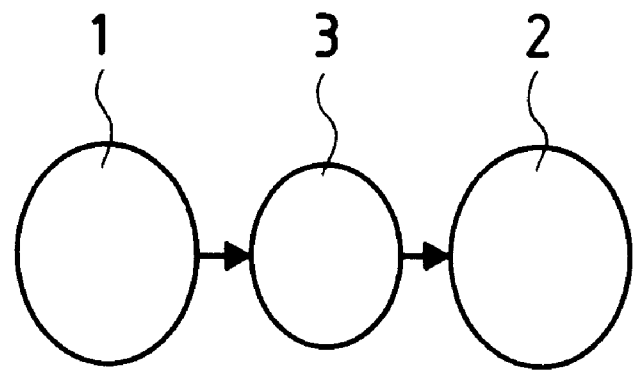
FIG. 1 shows a reaction system model which is utilized in a method for detection according to the invention and shows an interaction between reagents through a target substance.
Figure 2:
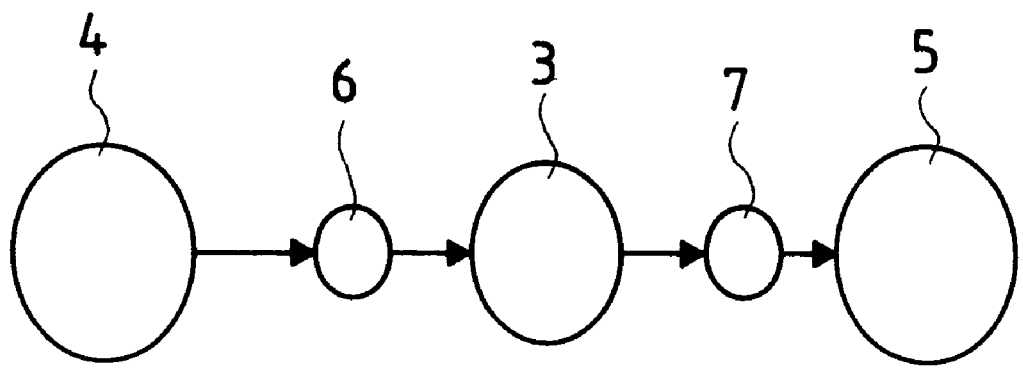
FIG. 2 shows a reaction system model which is utilized in a method for detection according to the invention and shows an interaction between reagents through a target substance.

FIGS. 1 and 2 typically show a reaction system model for causing the interaction according to the invention by way of an example of charge transfer. FIG. 1 shows a simplest reaction system comprising a target substance 3 (nucleic acid double helix structure) and two reagents 1 and 2 which are reactive with the substance 3. In this reaction system, charge is transferred from the reagent 1 (an electron donor) through the target substance 3 to the reagent 2 (an electron acceptor) in the direction of an arrow. The reaction system in the FIG. 2 further comprises reagents 6 and 7 added for mediating charge transfer in a reaction route in addition to reagents 4 and 5 for causing the interaction. Charge is also transferred in the direction of an arrow in this system. In the FIGS. 1 and 2, at least one of the reagents 1, 2, and 4 to 7 a re pyrylium compounds according to the invention. The number of the reagents is at least two, and is determined by considering efficiency of manipulation and sensitivity for detection. For the reagents 6 and 7, such substances as to function as mediator or sensitizer may be utilized. Further, at least on e substance mediating a reaction may be utilized as needed between each reaction substance in the reaction route shown in the FIG. 2, e.g., between the reagents 4 and 6, and between the reagent 6 and the target substance 3. Therefore, pyrylium compounds are utilized for at least one of reagents constructing the reaction route of the interaction, and are selected to have functions corresponding to the role in the reaction system for use. For example, the pyrylium compounds are utilized as an electron donor, an electron acceptor, a mediator, a sensitizer, etc.

Reagents for directly reacting with a double helix structure such as the reagents 1, 2, 6, and 7 in the FIGS. 1 and 2 preferably have properties as intercalator which specifically combine with the double helix structure. As the reagents, substances may be utilized which react with nucleic acids, etc. constructing the double helix structure to cause there chemical change, or cause the nucleic acid base to a chemical or a structural change. Alternatively, the substances may be utilized which react with a third substance further added to the reaction system in the presence of the double helix structure to cause another chemical or structural changes. In either case, detectable changes are caused by the interaction.

In the direct reaction, reactions such as charge or energy transfer between the nucleic acid constructive component forming the double helix structure and the reagent can be utilized. When charge transfer is utilized, reagent which is specifically inserted in the double helix structure and which functions as an electron donor or an electron acceptor against the constructive components of the nucleic acids.

For reactions based on the charge transfer, two cases are considered; reaction of through space and that of through bond. For the former through space case, two kinds of reactions are included: a case wherein an electron donor interactively reacts with an electron acceptor through π-stacks of DNA helix; and another case wherein the electron donor reacts with the electron acceptor due to proximity of a distance between two reagents accompanied with formation of the double helix structure. For the latter through bond case, charge transfer is considered to occur through bond of base, phosphoric acid moiety, and saccharide. In either case, reaction mechanism is not restricted thereto, as far as the above-mentioned direct reaction is derived from the formation of the double helix.

In the through space reaction utilizing π-stacks of DNA helix, the distance between an electron donor and an electron acceptor which are arranged to be capable of reacting with double helix structure (e.g. reagents 1 and 2 in the FIG. 1) is too large to react with each other, and an electron released from the electron donor is successively transferred to the neighboring nucleic acid base pair through an electron cloud spreading over the nucleic base pair, and finally transferred to the electron acceptor. Reversely, an electron is also considered to be pulled out from nucleic acid base pair by the electron acceptor in succession, and finally taken away from the electron donor. The nucleic acid base pair functions as a mediator for charge transfer.

On the other hand, in the through space reaction due to proximity of a distance between the electron donor and the electron acceptor, the distance between the electron donor and the electron acceptor is shortened by the formation of double helix structure so as to make their interaction possible. For example, the formation of double helix structure can be detected based on the interaction of the electron donor and the acceptor, by making the donor and the acceptor not to react with each other under the condition that both of the substances are single stranded and are sufficiently apart form each other in a solution, and by making both of the substances to react with each other when probe hybridize with a target nucleic acid to form a double helix structure and to make the electron donor to closely appear to the electron acceptor. When charge is hard to directly transfer from double helix structure to reagent, substances such as mediator or sensitizer may be arranged between the double helix structure and the reagent so as to mediate the charge transfer.

The reagents essentially need to be specifically arranged in the double helix structure of hybrid. Means for the reagents to be arranged at the position so as to react with the double helix structure include insertion of the reagents such as intercalator between the nucleic acid base pairs, embedding of the reagents in a groove of the double helix structure, arrangement of the reagents along with the double helix structure, etc.

Among these reagents, intercalator is most useful when charge transfer through stacking is utilized. Intercalator is generally compounds in plane having an electron area when inserted into nucleic acid, and is oriented, keeping the same distance as that between nucleic acid base pairs in such a manner as in a pile of nucleic acid base pairs. For example, when intercalator is utilized as an electron donor, and an electron acceptor is arranged at a position opposite to the electron donor through a double helix structure, an electron released from the electron donor can be transferred to the neighboring nucleic acid base pairs, through the π-electron cloud of the respective nucleic acid, and to the electron acceptor. Alternatively, when intercalator is utilized as an electron acceptor and an electron donor is arranged at a position opposite to the electron acceptor so that the electron donor faces to a double helix, charge transfer is conducted in the following mechanism: an electron is pulled out from nucleic acid base pairs by an electron hole on the electron acceptor, and an electron is successively pulled out from the next nucleic acid base pairs, finally pulled out from the electron donor. Therefore, for charge transfer through stacking, at least one of the electron donor and acceptor is preferably intercalator, and both of them are more preferably intercalator because efficiency of charge transfer can be elevated. Since intercalator is known to stabilize a double helix structure and to elevate its melting point, it is useful to utilize intercalator for the electron donor and acceptor for stabilization of hybrid between target nucleic acid and a probe.

According to the invention, a change caused by an interaction through a target substance is measured to detect the target substance. This change varies is changed dependently on the target substance and a reaction system comprising reagents for detecting the target substance and causing an interaction. In a method for detection, the variation is further dependent on components of the reaction system. For example, when a reaction system is utilized to cause an interaction based on charge transfer of reagents (e.g., reagents 1, 2, 4, and 5 in the FIGS. 1 and 2), the interaction of the reagents through a double helix structure can be measured as a change of an electron acceptor side by method appropriate for the change. Examples of the method are as follows: detection of appearance of a novel absorption spectrum or change of an absorption spectrum such as charge transfer absorption band; direct detection of coloring or discoloring of a solution of the reaction system as the result of the charge transfer (the change can be directly observed, and the reaction system is easy and useful); detection of reactions of appearance or disappearance of luminescence system from fluorescence and phosphorescence; detection of a chemical change of the electron acceptor due to the electron transfer; detection of a chemical luminiscence caused by a chemical reaction of the changed substance (the electron acceptor) and a third substance newly added; detection of biological luminescence by utilizing proteins such as enzyme and antibody as the third substance; and detection of a detectable change caused by the target substance itself.

The interaction is also detected by detecting a change of the electron donor side as well as a change of the electron acceptor side. The method for detecting a change of the electron acceptor side are basically applicable for a change of the electron donor side. When a fluorescence substance is utilized as an electron donor, it is possible to directly detect a change such as fluorescence disappearance by selecting a fluorescence substance which is reduced in quantum yield with charge transfer, and it is also possible to make the change visible by combining the variation with some reactions.

As mentioned above, any change based on the interaction may be detected according to the invention, as far as the change is caused by any reagents and a target substance constructing a reaction system. The change may be detected directly or indirectly by utilizing other reagents for detection.

Further, the following additional method may be utilized according to the invention: an electron donor may be activated with light to release an electron for charge transfer initiation; an electron donor may be stimulated with a third substance to generate an electron; and an electron acceptor may also be activated with initiating agents such as light (similar to those for an electron donor) to cause an electron to be pulled out from an electron donor.

As mentioned before, a third substance such as mediator or sensitizer which mediates charge transfer may be involved in addition to an electron donor and an electron acceptor. The third substance may be interactively reacted with a double helix to stimulate an electron donor and an electron acceptor to cause charge transfer which are not directly combined with a double helix.

In order to detect a target nucleic acid by means of hybridization with probe nucleic acid, change based on an interaction is measured or detected by detecting changes in chemical structure or property of pyrylium compounds and other compounds constructing reagents, or components of nucleic acid (target substance), in electronic condition, and in signals derived from substances changed by the interaction before and after the formation of the desired hybrid.

Examples of modes utilizing an electron donor and an electron acceptor are as follows:
(i) both of the donor and the acceptor are present at the time of forming a double helix structure by means of hybridization of probe and target nucleic acid;
(ii) both of the donor and the acceptor are added after the formation of a double helix structure by means of hybridization of probe and target nucleic acid; and
(iii) one of the donor and the acceptor is present at the time of formation of a double helix structure by means of hybridization of probe and target nucleic acid, and another is further added after the formation.

When energy transfer is utilized as an interaction, reagents include at least a set of an energy donor and an energy acceptor. The interaction of the donor and the acceptor is detected as change in chemical structure in electron conditions of the energy acceptor, the energy donor, or a third substance which can react with the two substances before and after the formation of hybrid, or as change in signals derived from changed substances. For example, hybrid can be detected by detecting reduction of fluorescence strength of the energy donor and increase of fluorescence strength of the energy acceptor. The change in the fluorescence strength is considered to be caused by the following mechanism: the energy donor and the energy acceptor are inserted into a double stranded chain moiety of hybrid in a mode of intercalator, etc.; the donor and the acceptor approach to each other; and an interaction can occur.

The energy donor and the energy acceptor may be utilized in the same manner of the above mentioned (i), (ii), and (iii) as that for an electron donor and an electron acceptor. As an initiation agent, light is mainly utilized.

The length of a probe utilized for detection of a target nucleic acid by means of hybridization according to the invention is determined for each case so that good hybridization with a target nucleic acid may be conducted and a stable double helix structure may be obtained. The length is preferably at least 8 bases, more preferably at least 12 bases so that reagents (e.g., reagents 1, 2, 6, and 7 in the FIGS. 1 and 2) utilized as an electron donor and an electron acceptor, or as an energy donor and an energy acceptor may be directly react with nucleic acid base to form a stable double helix structure.

Other than the length of a probe, base sequence itself, a salt concentration of a reaction system, and an ionic strength have also influences on stabilization of a double helix structure. For example, a sequence having more G-C base pairs than A-T base pairs forms a more stable double helix structure than that having a reverse ratio of G-C/A-T base pair, because G-C base pair has more hydrogen bonds than A-T base pair. Also, when the molecular concentration of KCl is elevated from 0.01M to 1M, the melting point of DNA is said to be increased by 30° C. Intercalator is largely effective for the stabilization of a double helix structure. Appropriate use of these stabilizing factors enable a probe of less than 8 base pairs to be utilized.

Properties of an electron donor and electron acceptor, and an energy donor and an energy acceptor should be also considered for selecting a probe. These reagents are not guaranteed to insert into any sequence of a double helix at a single probability. Specifically, reagents preferring G-C base paris to A-T base pairs are different in properties from those preferring vice versa. Therefore, when selecting a probe, the properties of the reagents should be also considered as well as the stability of a double helix consisting of a probe and a target nucleic acid.

A change caused by an interaction between an electron donor and an electron acceptor is preferably irreversible. Specifically, if an electron donor or an electron acceptor utilized for detection is changed irreversibly, the change based on the interaction can be accumulated and detected at high sensitivity.

Pyrylium compounds according to the invention are, compounds of the following formula [I]:

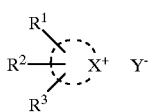

In the formula [I],

is a heterocyclic ring, and X is O, S, Se, or Te. Examples of the heterocyclic ring include five-membered or six-membered rings such as pyrylium ring or pyrylium-analogous ring.

$R^1$ and $R^2$ are independently hydrogen atom, halogen atom, sulphonate group, amino group, styryl group, nitro group, hydroxy group, carboxyl group, cyano group, substituted or non-substituted lower alkyl group, substituted or non-substituted aryl group, substituted or non-substituted lower aralkyl group, or substituted or non-substituted cycloalkyl group, $R^3$ is —A or —L—A, L is —$L^1$—, —$L^2$—$L^3$—, or —$L^4$—$L^5$—$L^6$—, and $L^1$ to $L^6$ are independently —(CH=CH)—, divalent group derived from substituted or non-substituted aryl group, substituted or non-substituted lower alkylene group, or —CH=$R^4$— ($R^4$ is cyclic ring having oxo group). The divalent group derived from substituted or non-substituted aryl group is, for example, phenylene group, which may be any of ortho, meta, and para. The lower alkylene group is, for example, straight or branched alkylene group having 1–4 carbons, which is substituted with —L—A, etc. The ring having oxo group is, for example, heterocyclic ring, aromatic ring, aliphatic ring, etc.

—L— is preferably the following [II], [III], [IV], [V], or [VI]:

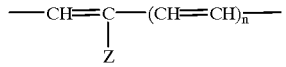

(In the formula [II], Z is hydrogen atom or substituted or non-substituted lower alkyl group, and n is 0, 1, or 2). When Z is alkyl group, it is substituted with the groups determined for —L—A.

(In the formula [III], n is 0, 1, or 2, and Φ is substituted or non-substituted o-, m-, or p-phenylene group).

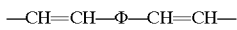

(In the formula [IV], Φ is substituted or non-substituted o-, m-, or p-phenylene group).

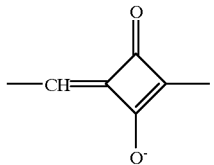

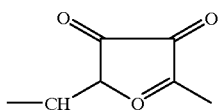

Substituents of phenylene group in the above-mentioned formula is, for example, the above-exemplified groups.

A of $R^3$ for the formula [I] is substituted or non-substituted aryl group, or —CH=$R^5$ ($R^5$ is substituted or non-substituted heterocyclic ring, substituted or non-substituted cycloalkyl group, or substituted or non-substituted aromatic ring). Heterocyclic ring of $R^5$ is, for example, groups derived from the following formulas:

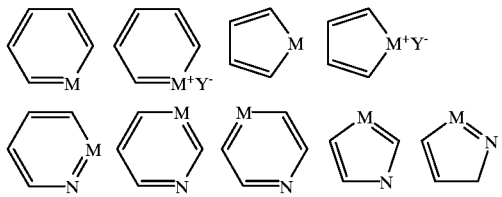

(M and N are independently oxygen atom, sulphur atom, or nitrogen atom, and $Y^-$ is anion), and the substituents are, for example, substituted or non-substituted aryl group. The substituted or non-substituted cycloalkyl group may be saturated or non-saturated, and is, for example, such group as derived from groups forming a resonance system of the followings:

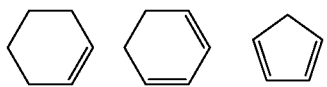

The substituted or non-substituted aromatic ring is, for example, azulene ring. Examples of the substituents for the aromatic ring are lower alkyl group, and substituted or non-substituted aryl group.

In pyrylium ring containing X or its analogous ring, the hydrogen atom combining with carbon atom to which none of $R^1$, $R^2$, and $R^3$ are combined may be substituted with halogen atom, sulphonate atom, amino group, styryl group, nitro group, hydroxyl group, carboxyl group, cyano group, substituted or non-substituted lower alkyl group, substituted or non-substituted aryl group, or substituted or non-substituted lower alalkyl group.

$Y^-$ is anion. Examples of the anion are $BF_4^-$, perchloric acid ion, $HO_3SCH_2COO^-$, halogen ion such as chlorine ion, bromine ion, iodine ion, and fluorine ion, compounds having an anion function such as aliphatic hydrocarbon and aromatic sulphonates, and complex ions of transition metals such as Zn, Ni, Cu, Pt, Co, and Pd.

When the above-mentioned substituents are further substituted with halogen atom, examples of the halogen atom are Cl, Br, and I. The lower alkyl group may be straight or branched, and has 1–4 carbons.

The compound [I] preferably has its X heterocyclic ring substituted with at least two substituted or non-substituted aryl group. For example, when the heterocyclic ring containing X is six-membered ring, in the compound [I]:

(1) the six-membered ring containing X is substituted at its 2 and 4 positions with substituted or non-substituted aryl group, and is substituted at any one of its 3, 5, and 6 positions with $R^3$;

(2) the six-membered ring containing X is substituted at its 3 and 5 positions with substituted or non-substituted aryl group, and is substituted at any one of its 2, 4, and 6 positions with $R^3$; and (3) the six-membered ring containing X is substituted at its 2 and 6 positions with substituted or non-substituted aryl group, and is substituted at any one of its 3, 4, and 5 positions with $R^3$.

The introduction of substituted or non-substituted aryl group into the above-mentioned positions is preferable in the fact that the pyrylium compounds so substituted are useful as intercalator for nucleic acid base pairs for detecting a double helix structure. In the heterocyclic ring containing X, it is further preferable that more than two substituted or non-substituted aryl groups are not arranged next to each other.

Either or both of at least two reagents which can form a reaction system causing a change based on an interaction mediated by a target substance is selected from the compounds of the general formula [I]. For detection of nucleic acids, the compounds [I] is preferably inserted into a double helix structure of nucleic acids as intercalator.

For detection of charge transfer, the compounds [I] having an electron donor group may be utilized as an electron donor. Examples of such compounds are those having its pyrylium ring or pyrylium-analogous ring substituted with aryl group which is substituted with amino group, etc. further substituted with lower alkyl group (lower alkylamino group). Examples of the lower alkylamino group include dimethyl amino group and diethylamino group which are substituted at their para positions. The substituted aryl group may directly substitute the pyrylium ring or pyrylium-analogous ring. For example, the aryl group may substitute lower alkyl group and form lower aralkyl group. Examples of the compounds utilized as an electron donor are shown in the following Table 1. Among the compounds shown in the Table 1, 2-methyl-4,6-bis-(4-N,N-dimethylaminophenyl) pyrylium salts and 2-methyl-4,6-bis-(4-N,N-dimethylaminophenyl)thiopyrylium salts are preferably utilized.

Compounds which can be utilized as an electron acceptor for the compounds shown in the Table 1 are, for example, shown in the following Table 2.

However, it is not determined that the compounds shown in the Table 1 are electron donors and those in the Table 2 are electron acceptors. The compounds are not unconditionally determined to be electron donors or electron acceptors, but relatively determined based on their oxidization/reduction potentials, etc. Therefore, a set of an electron donor and acceptor may be selected within the compounds in the Table 1, and also in the Table 2. A set of an electron donor and acceptor may also be selected from pyrylium compounds shown in the Table 1 and other reagents, and from pyrylium compounds shown in the Table 2 and other reagents. Further, a set of an electron donor and acceptor is selected from other reagents, and pyrylium compounds may be additionally utilized as mediator or sensitizer.

For energy transfer, it is most important that the energy level of an energy donor is almost the same as that of an energy acceptor; energy transfer is considered to be caused by the approaching of both of the donor and acceptor after they are inserted into a target substance such as a nucleic acid double helix structure. Among the pyrylium compounds shown in the Table 1, such a compound as having an increased fluorescence strength at the time of insertion into a nucleic acid double helix and as maintaining a stable excited condition may be utilized as an energy donor. It is preferable to select an energy acceptor which corresponds to the respective fluorescence energy level. Also, for energy transfer, both of the donor and the acceptor may be selected from pyrylium compounds, and a set of pyrylium compound and reagent other than the pyrylium compounds may be utilized, which is similar to a charge transfer.

When compounds other than pyrylium compounds are utilized as one of reagents, any compounds may be utilized as far as an objective detection can be conducted by utilizing the compounds according to the invention. Examples of an electron acceptor for charge transfer are 4,4-dimethyloxazolidine-N-oxyl (DOXXL) as a spin labeling agent, 2,2,5,5-tetramethylpyrolidine-N-oxyl(PROXL), 2,2,6,6-tetramethylpiperidine-N-oxyl), and their derivatives. Riboflavin, N,N-dimethyl-2,7-diazapyrenium ion, and their derivatives may also be utilized.

Examples of compounds other than pyrylium compounds which may be utilized as an electron donor include acridine, anthracene, pyrene, ethydium bromide, proflavin, porphyrin, thiazol orange dimer (TOTO), oxazole yellow (YOYO), 4,6-diamino-2-phenylindole dihydrochloride, and propidium iodide (PI).

Fluorescence dyes generally utilized such as cyanin, azulene, dansyl, fluorescein, eosine, rhodamine, and their derivatives may also be utilized.

Compounds other than the pyrylium compounds described above are not absolutely determined as electron donors or acceptors, but relatively evaluated for their oxidation/reduction potentials in relative to other reagents simultaneously utilized, and utilized as electron donors, electron acceptors, mediators, sensitizers, etc.

Next, a preferable embodiment of the invention utilizing reagents combined with probe is described.

By combining reagents with probe, an interaction between reagents through no nucleic acids can be excluded, resulting in increased S/N ratio. Further, by utilizing pyrylium compounds according to the invention which largely vary in fluorescence property between in free condition and in nucleic acid combining condition, background due to the pyrylium compounds either in free or in combined with probe can be excluded.

The most preferred mode for combining reagents with probe is that both of an electron donor and acceptor, or both of an energy donor and an energy acceptor are combined with probe. In this mode, the positional relation between reagents interactively reacted is made apparent, and the interaction can be advantageously controlled by adjusting the positional relation on probe. The distance between an electron donor and an electron acceptor or between an energy donor and an energy acceptor is determined according to kinds of the utilized reagents. For example, when the approaching effect is utilized, the distance is preferably 20 to 120 Angstrom, more preferably 50 to 80 Angstrom at the time of forming a double helix structure of hybrid. When charge transfer through a double helix structure is utilized, the distance is determined by considering structural changes such as unwinding caused by each of the reagents, and is preferably 20 to 120 Angstrom. However, the distance is varied according to the conditions, for example, that both of an electron donor and acceptor are intercalator or that either or both of them are inserted into a major groove or a minor groove, and is not therefore restricted to said length. It is noted that the distance is more preferably 50 to 80 Angstrom because charge transfer between an electron donor and acceptor through no nucleic acid can occur when the distance is too short.

The length of a probe is so determined that good hybridization with a target nucleic acid and a stable double helix structure are obtained. When both of an electron donor and acceptor or an energy donor and acceptor are combined with probe, and they can interactively react with each other in the condition that they closely approach to each other even in the absence of double helix structure, the length of a probe is determined by considering the distance between reagents, and is at least 8 bases, and is more preferably at least 12 bases.

Other than the length of a probe, base sequence itself, a salt concentration of a reaction system, and an ionic strength have also influences on stabilization of a double helix structure. For example, a sequence having more G-C base pairs than A-T base pairs forms a more stable double helix structure than that having a reverse ratio of G-C/A-T base pair, because G-C base pair has more hydrogen bonds than A-T base pair. Also, when the molecular concentration of KCl is elevated from 0.01M to 1M, the melting point of DNA is said to be increased by 30° C. Intercalator is largely effective for the stabilization of a double helix structure. Appropriate use of these stabilizing factors enable a probe of less than 8 base pairs to be utilized.

Here is described modes of electron donor and acceptor, and energy donor and acceptor according to the invention. When one of the donor and acceptor is combined with a probe, either of the following mode is utilized:

a) when a probe combined with one of the donor and acceptor is hybridized with a target nucleic acid to form a double helix structure, another of the donor and acceptor also resides in a reaction system, and is made to interact after the formation, or b) After a probe combined with one of the donor and acceptor is hybridized with a target nucleic acid to form a double helix structure, another of the donor and acceptor is added to a reaction system, and is made to interact after the formation.

When both of the donor and acceptor are combined with probe, both of them reside in a reaction system at the time of hybridization of a probe and a target nucleic acid, and are made to interact each other after the formation of hybrid.

According to the invention, the following modes are utilized in order to combine probe with reagents containing pyrylium compounds (a set of an electron donor and acceptor, or an energy donor and acceptor):

a) one of the probe is combined with pyrylium compounds which are electron donors or energy donors, and electron acceptor or energy acceptor which specifically interact with a double helix are added in free condition;

b) one of the probe is combined with pyrylium compounds which are electron acceptors or energy acceptors, and electron donor or energy donor which specifically interact with a double helix are added in free condition;

c) one of the probe is combined with reagents which are electron donors or energy donors, and pyrylium compounds which are electron acceptor or energy acceptor and specifically interact with a double helix are added in free condition;

d) one of the probe is combined with reagents which are electron acceptors or energy acceptors, and pyrylium compounds which are electron donors or energy donor and specifically interact with a double helix are added in free condition; and e) each of pyrylium compounds of two kinds which form a set of an electron donor and an electron acceptor, or an energy donor and an energy acceptor is combined with probe, and f) a combination of pyrylium compounds and other reagents which form a set of an electron donor and an electron acceptor, or an energy donor and an energy acceptor is combined with probe.

EXAMPLES

The present invention will now be described in detail by way of reference examples and examples.

Reference Example 1

Anhydrous acetic acid (100 ml) and condensed sulphuric acid (30 ml) were mixed by cooling, and the resulting mixture solution was maintained at 80° C. in a water bath. To the mixture, anhydrous acetic acid (20 ml) and p-dimethylaminoacetophenone (30 ml) were added at room temperature. The resulting mixture was then heated to 45° C., and stirred for 24 hours for reaction. To the reacted solution, ethanol of an equivalent amount was added, followed by cooling. To the cooled solution, potassium iodide was further added to precipitate a crude crystal. The crude crystal was collected by filtration, and recrystallized with a mixture solvent of ethanol/ether (volume ratio: 1:4) to obtain 2-methyl-4,6-bis-(4-N,N-dimethylaminophenyl)pyrylium iodide (a compound 1 in the Table 1, wherein Y is I) of green crystal.

Analysis of the compound 1 (Y:I)

melting point: 254–257° C. UV/visible ($CH_3CN$ $\epsilon \times 10^{-4}$) $\lambda$max: 444 nm(2.43), 550 nm(8.24); NMR($^1$H, DMSO) $\delta$ ppm: 8.3737 (1H, s), 8.2729 (1H, d, J=9.0 Hz), 8.1795 (1H, d, J=9.0 Hz), 7.8864 (1H, s), 6.9117 (4H, t, $J_{AB}=J_{BC}=9.77$), 3.1829 (6H, s), 3.1340 (6H, s), 2.6809 (3H, s); FAB mass m/z 333; IR(KBr) $v cm^-$: 1645, 1610(sh), 1580(s), 1490(s), 1270, 1200, 1160.

Further, 2-methyl-4,6-bis-(4-N,N-dimethylaminophenyl) pyrylium perchlorate (compound 1 (Y: $ClO_4$)) was prepared in the same manner as said with the exception that potassium iodide was replaced with perchloric acid solution.

Reference Example 2

Sodium sulphide ($Na_2S.9H_2O$)(20 g) was dissolved in ion exchange water to prepare a solution of a total amount of 50 ml. To the solution, sodium hydrogencarbonate (7 g) was added for dissolution, followed by cooling on ice. To the solution, ethanol (50 ml) was further added, followed by stirring at room temperature for 30 minutes. The precipitated sodium carbonate was separated by filtration, and washed with ethanol (25 ml). The filtrate was mixed with the wash liquid to obtain a mixture solution (ca. 125 ml) of water and ethanol containing sodium hydrosulphide.

Next, 2-methyl-4,6-bis-(4-N,N-dimethylaminophenyl) pyrilium iodide (0.92 g) was dissolved in DMSO (20 ml). To the solution, the mixture solution of water and ethanol containing sodium hydrosulphide prepared as said (5 ml) was added, followed by stirring at room temperature for five minutes. To the resulting solution, hydriodic acid (0.75 ml) was further added, followed by stirring for five minutes. The mixture solution was then extracted with dichloromethane, purified through a silica gel column, and recrystallized with a mixture solution of ethanol/ether (volume ratio, 1:4) according to a general method to obtain a crystal of 2-methyl-4,6-bis-(4-N,N-dimethylaminophenyl) thiopyrylium iodide (a compound 2 in the Table 1 (Y=I)). Analysis of the compound 2 (Y:I)

melting point: 246–248° C. UV/visible (CH$_3$CN $\epsilon \times 10^{-4}$) λmax: 495 nm (2.50), 587 nm (4.95); NMR($^1$H, DMSO) δ ppm: 8.5679 (1H, s), 8.4323 (1H, s), 8.2436 (2H, d, J=9.27 Hz), 7.9786 (2H, d, J=9.28), 6.8959 (4H, t, J$_{AB}$=J$_{BC}$=9.28), 3.1756 (6H, s), 3.1157 (6H, s), 2.8323 (3H, s); FAB mass m/z 349; IR(KBr) vcm$^{-1}$: 1600 (s), 1560 (s), 1460 (s), 1430 (s), 1370 (s), 1260 (s), 1160 (s).

Further, 2-methyl-4,6-bis-(4-N,N-dimethylaminophenyl) thiopyrylium perchlorate (the compound 2 (Y:ClO$_4$)) was prepared in the same manner as said with the exception that hydriodic acid was replaced with perchloric acid.

Reference Example 3

Compounds 3–55 shown in the Table 1 were prepared. In the Table 1, Φ is p-phenylene group:

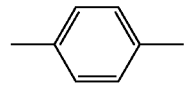

or phenyl group.

TABLE 1

| Compound No. | X | Y | R$_i$ | L | A |
|---|---|---|---|---|---|
| 1 | O | ClO$_4$ or I | R$_6$ = CH$_3$<br>R$_7$ = H<br>R$_8$ = Φ-N(CH$_3$)$_2$<br>R$_9$ = H<br>R$_{10}$ = A | | Φ-N(CH$_3$)$_2$ |
| 2 | S | ClO$_4$ or I | R$_6$ = CH$_3$<br>R$_7$ = H<br>R$_8$ = Φ-N(CH$_3$)$_2$<br>R$_9$ = H<br>R$_{10}$ = A | | Φ-N(CH$_3$)$_2$ |
| 3 | O | ClO$_4$ or I | R$_6$ = Φ<br>R$_7$ = H<br>R$_8$ = A<br>R$_9$ = H<br>R$_{10}$ = Φ | | Φ-N(CH$_3$)$_2$ |
| 4 | S | ClO$_4$ or I | R$_6$ = Φ<br>R$_7$ = H<br>R$_8$ = A<br>R$_9$ = H<br>R$_{10}$ = Φ | | Φ-N(CH$_3$)$_2$ |
| 5 | O | ClO$_4$ or I | R$_6$ = Φ<br>R$_7$ = H<br>R$_8$ = L-A<br>R$_9$ = H<br>R$_{10}$ = Φ | general formula [II]<br>n = 0<br>Z = H | Φ-N(CH$_2$CH$_3$)$_2$ |
| 6 | S | ClO$_4$ or I | R$_6$ = Φ<br>R$_7$ = H<br>R$_8$ = L-A<br>R$_9$ = H<br>R$_{10}$ = Φ | general formula [II]<br>n = 0<br>Z = H | Φ-N(CH$_2$CH$_3$)$_2$ |
| 7 | O | ClO$_4$ or I | R$_6$ = Φ<br>R$_7$ = H<br>R$_8$ = Φ<br>R$_9$ = H<br>R$_{10}$ = L-A | general formula [II]<br>n = 0<br>Z = H | Φ-N(CH$_3$)$_2$ |
| 8 | S | ClO$_4$ or I | R$_6$ = Φ<br>R$_7$ = H<br>R$_8$ = Φ<br>R$_9$ = H<br>R$_{10}$ = L-A | general formula [II]<br>n = 0<br>Z = H | Φ-N(CH$_3$)$_2$ |
| 9 | O | ClO$_4$ or I | R$_6$ = Φ<br>R$_7$ = H<br>R$_8$ = L-A<br>R$_9$ = H<br>R$_{10}$ = Φ | general formula [II]<br>n = 1<br>Z = H | Φ-N(CH$_3$)$_2$ |
| 10 | S | ClO$_4$ or I | R$_6$ = Φ | general formula [II] | Φ-N(CH$_3$)$_2$ |

TABLE 1-continued

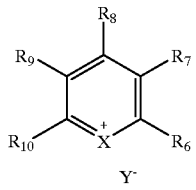

| Compound No. | X | Y | $R_i$ | L | A |
|---|---|---|---|---|---|
| | | | $R_7 = H$ | n = 1 | |
| | | | $R_8 = L-A$ | Z = H | |
| | | | $R_9 = H$ | | |
| | | | $R_{10} = \Phi$ | | |
| 11 | O | $ClO_4$ or I | $R_6 = \Phi$ | general formula [II] | $\Phi-N(CH_3)_2$ |
| | | | $R_7 = H$ | n = 1 | |
| | | | $R_8 = L-A$ | Z = | |
| | | | $R_9 = H$ | $(-)CH{=}CH-\Phi-$ | |
| | | | $R_{10} = \Phi$ | $N(CH_3)_2$ | |
| 12 | S | $ClO_4$ or I | $R_6 = \Phi$ | general formula [II] | $\Phi-N(CH_3)_2$ |
| | | | $R_7 = H$ | n = 1 | |
| | | | $R_8 = L-A$ | Z = | |
| | | | $R_9 = H$ | $(-)CH{=}CH-\Phi-$ | |
| | | | $R_{10} = \Phi$ | $N(CH_3)_2$ | |
| 13 | O | $ClO_4$ or I | $R_6 = \Phi$ | general formula [III] | $\Phi-N(CH_3)_2$ |
| | | | $R_7 = H$ | n = 1 | |
| | | | $R_8 = L-A$ | | |
| | | | $R_9 = H$ | | |
| | | | $R_{10} = \Phi$ | | |
| 14 | S | $ClO_4$ or I | $R_6 = \Phi$ | general formula [III] | $\Phi-N(CH_3)_2$ |
| | | | $R_7 = H$ | n = 1 | |
| | | | $R_8 = L-A$ | | |
| | | | $R_9 = H$ | | |
| | | | $R_{10} = \Phi$ | | |
| 15 | O | $ClO_4$ or I | $R_6 = \Phi$ | general formula [IV] | $\Phi-N(CH_2CH_3)_2$ |
| | | | $R_7 = H$ | | |
| | | | $R_8 = L-A$ | | |
| | | | $R_9 = H$ | | |
| | | | $R_{10} = \Phi$ | | |
| 16 | S | $ClO_4$ or I | $R_6 = \Phi$ | general formula [IV] | $\Phi-N(CH_2CH_3)_2$ |
| | | | R= H | | |
| | | | $R_8 = L-A$ | | |
| | | | $R_9 = H$ | | |
| | | | $R_{10} = \Phi$ | | |
| 17 | O | $ClO_4$ or I | $R_6 = \Phi$ | general formula [IV] | $\Phi-N(CH_2CH_3)_2$ |
| | | | $R_7 = H$ | | |
| | | | $R_8 = \Phi$ | | |
| | | | $R_9 = H$ | | |
| | | | $R_{10} = L-A$ | | |
| 18 | S | $ClO_4$ or I | $R_6 = \Phi$ | general formula [IV] | $\Phi-N(CH_2CH_3)_2$ |
| | | | $R_7 = H$ | | |
| | | | $R_8 = \Phi$ | | |
| | | | $R_9 = H$ | | |
| | | | $R_{10} = L-A$ | | |
| 19 | O | $ClO_4$ or I | $R_6 = \Phi$ | general formula [V] | 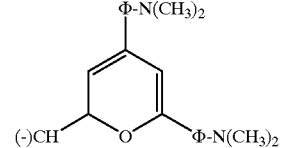 |
| | | | $R_7 = H$ | | |
| | | | $R_8 = \Phi$ | | |
| | | | $R_9 = H$ | | |
| | | | $R_{10} = L-A$ | | |
| 20 | S | $ClO_4$ or I | $R_6 = \Phi$ | general formula [V] | 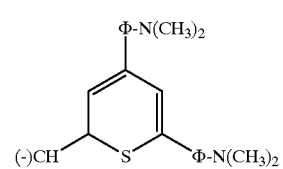 |
| | | | $R_7 = H$ | | |
| | | | $R_8 = \Phi$ | | |
| | | | $R_9 = H$ | | |
| | | | $R_{10} = L-A$ | | |

TABLE 1-continued

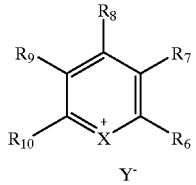

| Compound No. | X | Y | R$_i$ | L | A |
|---|---|---|---|---|---|
| 21 | O | ClO$_4$ or I | R$_6$ = Φ<br>R$_7$ = H<br>R$_8$ = Φ<br>R$_9$ = H<br>R$_{10}$ = L-A | general formula [V] | 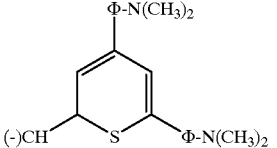 |
| 22 | O | ClO$_4$ or I | R$_6$ = Φ<br>R$_7$ = H<br>R$_8$ = Φ<br>R$_9$ = H<br>R$_{10}$ = L-A | general formula [VI] | 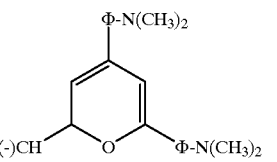 |
| 23 | S | ClO$_4$ or I | R$_6$ = Φ<br>R$_7$ = H<br>R$_8$ = Φ<br>R$_9$ = H<br>R$_{10}$ = L-A | general formula [VI] | 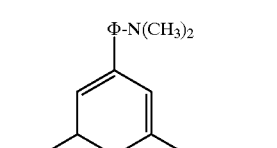 |
| 24 | O | ClO$_4$ or I | R$_6$ = Φ<br>R$_7$ = H<br>R$_8$ = Φ<br>R$_9$ = H<br>R$_{10}$ = L-A | general formula [VI] | 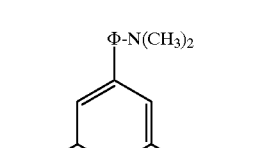 |
| 25 | O | ClO$_4$ or I | R$_6$ = Φ<br>R$_7$ = H<br>R$_8$ = Φ<br>R$_9$ = H<br>R$_{10}$ = L-A | general formula [II]<br>n = 0<br>Z = H | 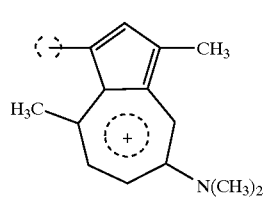 |
| 26 | S | ClO$_4$ or I | R$_6$ = Φ<br>R$_7$ = H<br>R$_8$ = Φ<br>R$_9$ = H<br>R$_{10}$ = L-A | general formula [II]<br>n = 0<br>Z = H | 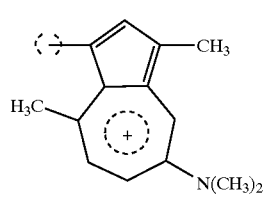 |

TABLE 1-continued

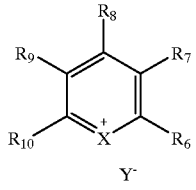

| Compound No. | X | Y | $R_i$ | L | A |
|---|---|---|---|---|---|
| 27 | O | $ClO_4$ or I | $R_6 = \Phi$<br>$R_7 = H$<br>$R_8 = \Phi$<br>$R_9 = H$<br>$R_{10} = L$-A | general formula [II]<br>n = 0<br>Z = H | 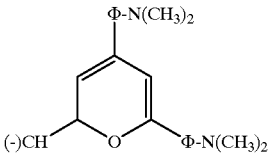 |
| 28 | S | $ClO_4$ or I | $R_6 = \Phi$<br>$R_7 = H$<br>$R_8 = \Phi$<br>$R_9 = H$<br>$R_{10} = L$-A | general formula [II]<br>n = 0<br>Z = H | 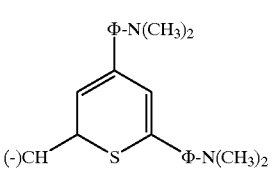 |
| 29 | O | $ClO_4$ or I | $R_6 = \Phi$<br>$R_7 = H$<br>$R_8 = \Phi$<br>$R_9 = H$<br>$R_{10} = L$-A | general formula [II]<br>n = 0<br>Z = H | 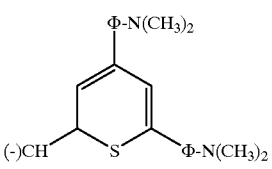 |
| 30 | O | $ClO_4$ or I | $R_6 = \Phi$<br>$R_7 = H$<br>$R_8 = L$-A<br>$R_9 = H$<br>$R_{10} = \Phi$ | general formula [II]<br>n = 0<br>Z = H | 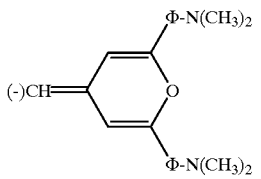 |
| 31 | S | $ClO_4$ or I | $R_6 = \Phi$<br>$R_7 = H$<br>$R_8 = L$-A<br>$R_9 = H$<br>$R_{10} = \Phi$ | general formula [II]<br>n = 0<br>Z = H | 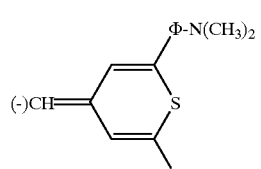 |
| 32 | O | $ClO_4$ or I | $R_6 = \Phi$<br>$R_7 = H$<br>$R_8 = L$-A<br>$R_9 = H$<br>$R_{10} = \Phi$ | general formula [II]<br>n = 0<br>Z = H | 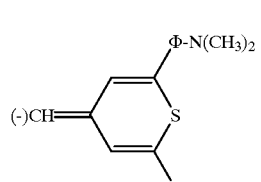 |
| 33 | O or S | $ClO_4$ or I | $R_6 = \Phi$-$N(CH_3)_2$<br>$R_7 = H$<br>$R_8 = A$<br>$R_9 = H$<br>$R_{10} = \Phi$-$N(CH_3)_2$ | | $\Phi$-$N(CH_3)_2$ |
| 34 | same as the above | same as the above | same as the above | | —$CH_3$ |
| 35 | same as the above | same as the above | same as the above | | $\Phi$-COOH |
| 36 | O or S | $ClO_4$ or I | $R_6 = \Phi$-$N(CH_3)_2$<br>$R_7 = H$<br>$R_8 = L$-A | general formula [II]<br>n = 0<br>Z = H | $\Phi$-$N(CH_3)_2$ |

TABLE 1-continued

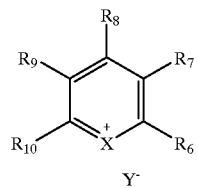

| Compound No. | X | Y | $R_i$ | L | A |
|---|---|---|---|---|---|
| 37 | same as the above | same as the above | $R_9 = H$<br>$R_{10} = \Phi\text{-}N(CH_3)_2$<br>same as the above | general formula [II]<br>n = 1<br>z = H | $\Phi\text{-}N(CH_3)_2$ |
| 38 | same as the above | same as the above | same as the above | general formula [III]<br>n = 1 | $\Phi\text{-}N(CH_3)_2$ |
| 39 | O or S | $ClO_4$ or I | $R_6 = \Phi\text{-}N(CH_3)_2$<br>$R_7 = H$<br>$R_8 = L\text{-}A$<br>$R_9 = H$<br>$R_{10} = \Phi\text{-}N(CH_3)_2$ | general formula [IV] | $\Phi\text{-}N(CH_3)_2$ |
| 40 | same as the above | same as the above | same as the above | general formula [II]<br>n = 0<br>Z = H | $\Phi\text{-}COOH$ |
| 41 | same as the above | same as the above | same as the above | general formula [II]<br>n = 1<br>Z = H | $\Phi\text{-}COOH$ |
| 42 | O or S | $ClO_4$ or I | $R_6 = \Phi\text{-}N(CH_3)_2$<br>$R_7 = H$<br>$R_8 = L\text{-}A$<br>$R_9 = H$<br>$R_{10} = \Phi\text{-}N(CH_3)_2$ | general formula [III]<br>n = 1 | $\Phi\text{-}COOH$ |
| 43 | same as the above | same as the above | same as the above | general formula [IV] | $\Phi\text{-}COOH$ |
| 44 | same as the above | same as the above | $R_6 = L\text{-}A$<br>$R_7 = H$<br>$R_8 = \Phi\text{-}N(CH_3)_2$<br>$R_{9 = H}$<br>$R_{10} = \Phi\text{-}N(CH_3)_2$ | general formula [II]<br>n = 0<br>Z = H | $\Phi\text{-}N(CH_3)_2$ |
| 45 | O or S | $ClO_4$ or I | $R_6 = L\text{-}A$<br>$R_7 = H$<br>$R_8 = \Phi\text{-}N(CH_3)_2$<br>$R_9 = H$<br>$R_{10} = \Phi\text{-}N(CH_3)_2$ | general formula [II]<br>n = 1<br>Z = H | $\Phi\text{-}N(CH_3)_2$ |
| 46 | same as the above | same as the above | same as the above | general formula [III]<br>n = 1 | $\Phi\text{-}N(CH_3)_2$ |
| 47 | same as the above | same as the above | same as the above | general formula [IV] | $\Phi\text{-}N(CH_3)_2$ |
| 48 | O or S | $ClO_4$ or I | $R_6 = L\text{-}A$<br>$R_7 = H$<br>$R_{8 = \Phi\text{-}N(CH3)_2}$<br>$R_9 = H$<br>$R_{10} = \Phi\text{-}N(CH_3)_2$ | general formula [II]<br>n = 0<br>Z = H | $\Phi\text{-}COOH$ |
| 49 | same as the above | same as the above | same as the above | general formula [II]<br>n = 1<br>Z = H | $\Phi\text{-}COOH$ |
| 50 | same as the above | same as the above | same as the above | general formula [III]<br>n = 1 | $\Phi\text{-}COOH$ |
| 51 | O or S | $ClO_4$ or I | $R_6 = L\text{-}A$<br>$R_7 = H$<br>$R_8 = \Phi\text{-}N(CH_3)_2$<br>$R_9 = H$<br>$R_{10} = \Phi\text{-}N(CH_3)_2$ | general formula [IV] | $\Phi\text{-}COOH$ |
| 52 | same as the above | same as the above | $R_6 = A$<br>$R_7 = H$<br>$R_8 = \Phi\text{-}N(CH_3)_2$<br>$R_9 = H$<br>$R_{10} = \Phi\text{-}N(CH_3)_2$ | | —COOH |
| 53 | same as the above | same as the above | same as the above | | $\Phi\text{-}COOH$ |
| 54 | O or S | $ClO_4$ or I | $R_6 = \Phi$<br>$R_7 = H$<br>$R_8 = \Phi\text{-}N(CH_3)_2$<br>$R_9 = H$<br>$R_{10} = \Phi\text{-}N(CH_3)_2$ | | |

TABLE 1-continued

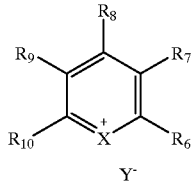

| Compound No. | X | Y | $R_i$ | L | A |
|---|---|---|---|---|---|
| 55 | same as the above | same as the above | $R_6 = \Phi\text{-}N(CH_3)_2$<br>$R_7 = H$<br>$R_8 = \Phi$<br>$R_9 = H$<br>$R_{10} = \Phi\text{-}N(CH_3)_2$ | | |

The compound 7 was obtained by synthesizing a compound [i]:

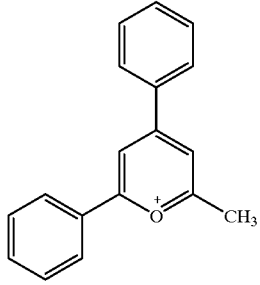

[i]

by reacting the compound [i] with (p-N,N-dimethylaminobenzaldehyde):

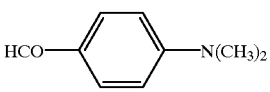

and by finally reacting the resulting compound with a desired anion, according to the method of W. Forest et al. (*New Methods of Preparative Organic Chemistry*, Acad. Press, 1964). The compound 17 was obtained by reacting the compound [i] with (p-diethylaminostyrylbenzaldehyde):

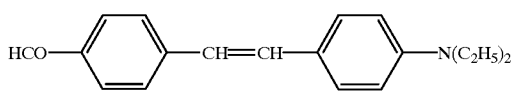

and by further reacting the resulting compound with a desired anion. The compounds 8 and 18 were synthesized by reacting the compound [i] with sodium hydrosulphide, and by treating the resulting compound [ii] according to the same manner as for the compounds 7 and 17.

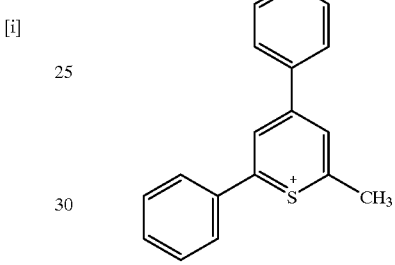

[ii]

The compound [iii]:

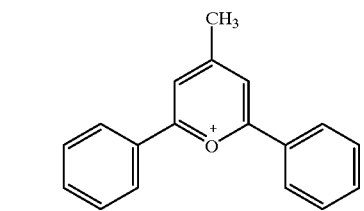

[iii]

was synthesized from acetophenone and acetoaldehyde through the following route:

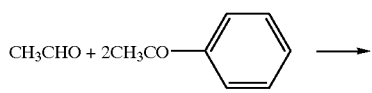

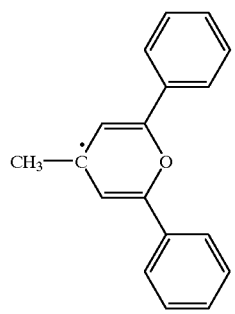

according to the method of R. Wizinger et al. (*Helv. chim. Acta*, 39, 217, 1956). By utilizing the compound [iii] as a material, the four compounds 5, 15, 9, and 11 were obtained as follows; the compound 5 was obtained by reacting the compound [iii] with p-dimethylaminobenzaldehyde and by further reacting the resulting compound with anion; the compound 15 was obtained by reacting the compound [iii] with p-diethylaminostyrylbenzaldehyde; the compound 9 was obtained by reacting the compound [iii] with p-dimethylamino aldehyde cinnamate; the compound 11 was obtained by reacting the compound [iii] with the following compound:

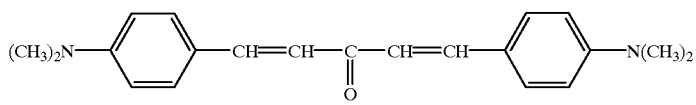

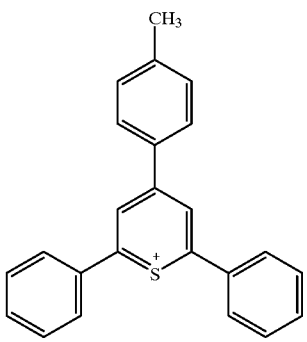

[vi]

Also, the compounds 6, 16, 10, and 12 were obtained by reacting the compound [iii] with sodium hydrosulphide, and by treating the resulting compound [iv] according to the same manner for the compounds 5, 15, 9, and 11 with the exception that the compound [iii] was replaced with the compound [iv].

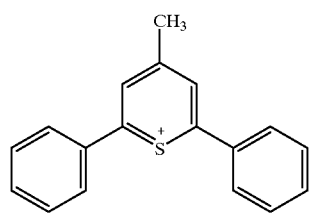

[iv]

Further, the compound 4 was obtained by preparing a cation part of the compound 3 according to the same manner for the compound [iii] with the exception that acetoaldehyde was replaced with p-dimethylaminobenzaldehyde, by reacting a cation part with sodium hydrosulphide, and by further reacting the resulting compound with a desired anion. Also, the compound [vi]:

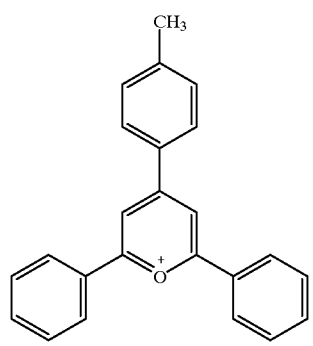

[v]

was obtained by reacting p-methylbenzaldehyde with acetophenone, and by reacting the resulting compound [v]:

with sodium hydrosulphide. Further, the compounds 13 was obtained by reacting the compound [v] with p-dimethylaminobenzaldehyde, and the compound 14 was obtained by reacting the compound [vi] with p-dimethylaminobenzaldehyde.

The compounds 19, 20, and 21 were obtained by reacting a cation of the compound [i], [ii], the compound 1, or the compound 2 with the following compound,

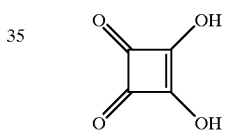

and by further reacting the resulting compound with anion. The compounds 22, 23, and 24 were obtained by reacting a cation part of the compound [i], [ii], the compound 1, or the compound 2 with the following compound:

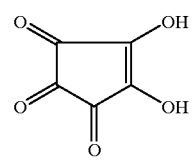

and by reacting the resulting compound with a desired anion. The compounds 25 and 26 were obtained by reacting the compound [i] or [ii] with the following compound:

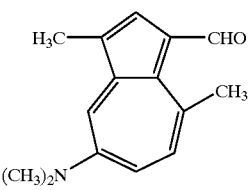

and by reacting the compound with a desired anion. The compounds 27, 28, and 29 were obtained by reacting a cation part of the compound [i], [ii], the compound 1, or the compound 2 with triethoxymethane [$HC(OC_2H_5)_3$], and reacting the resulting compound with a desired anion. The compounds 30, 31, and 32 were obtained by reacting the compound [iii] synthesized from p-dimethylaminoacetophenone and dimethylamino derivatives of the compound [iv] with triethoxymethane, and by reacting the resulting compound with a desired anion according to the same manner for the compounds [iii] and [iv].

The compounds 33–55 were obtained by the following reactions, respectively.

Synthesis of Compound 33

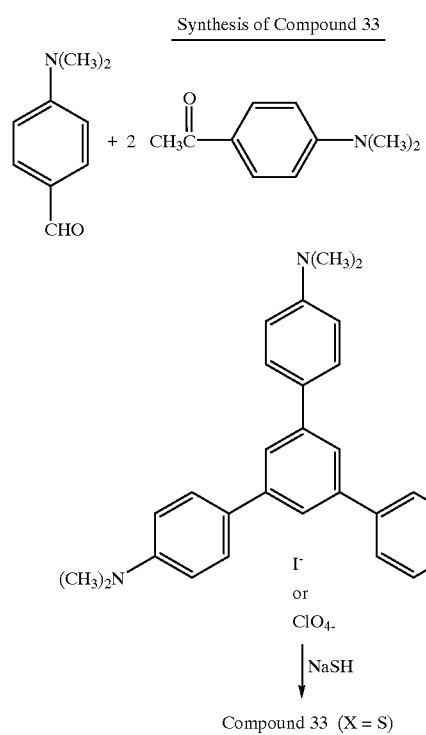

Synthesis of Compound 34

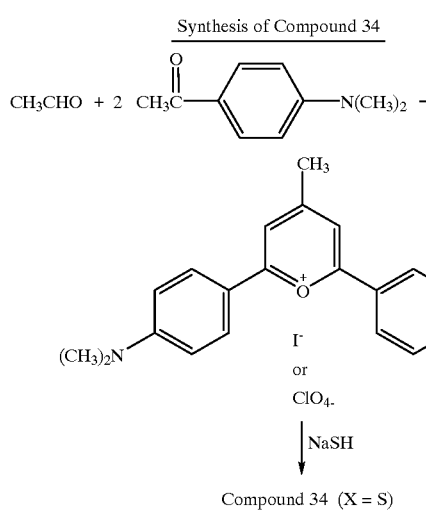

Synthesis of Compound 35

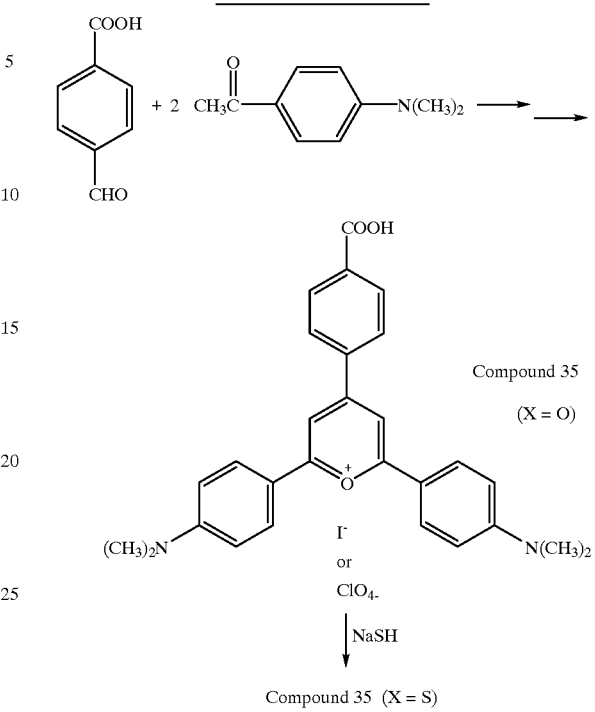

Synthesis of Compound 36

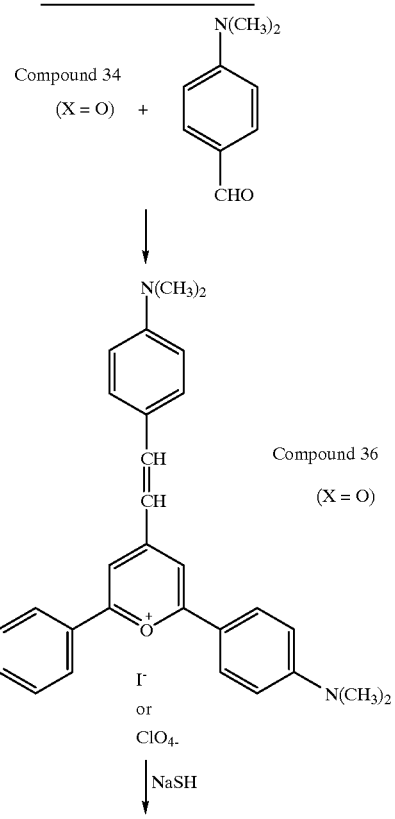

Synthesis of Compound 37
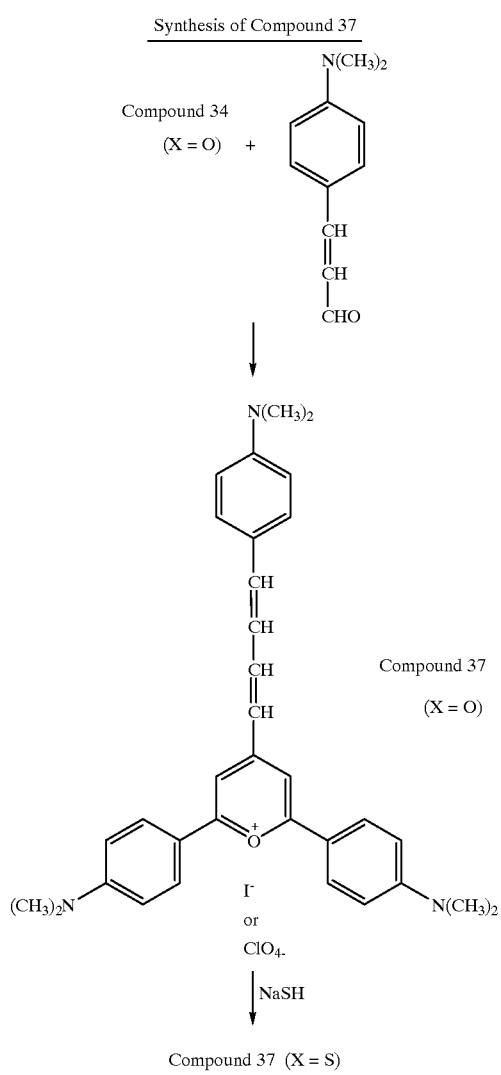
Synthesis of Compound 38
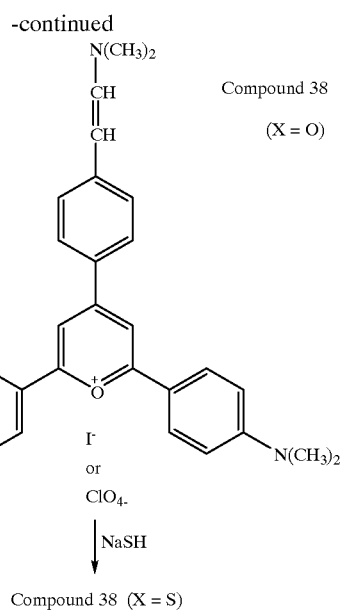
Synthesis of Compound 39
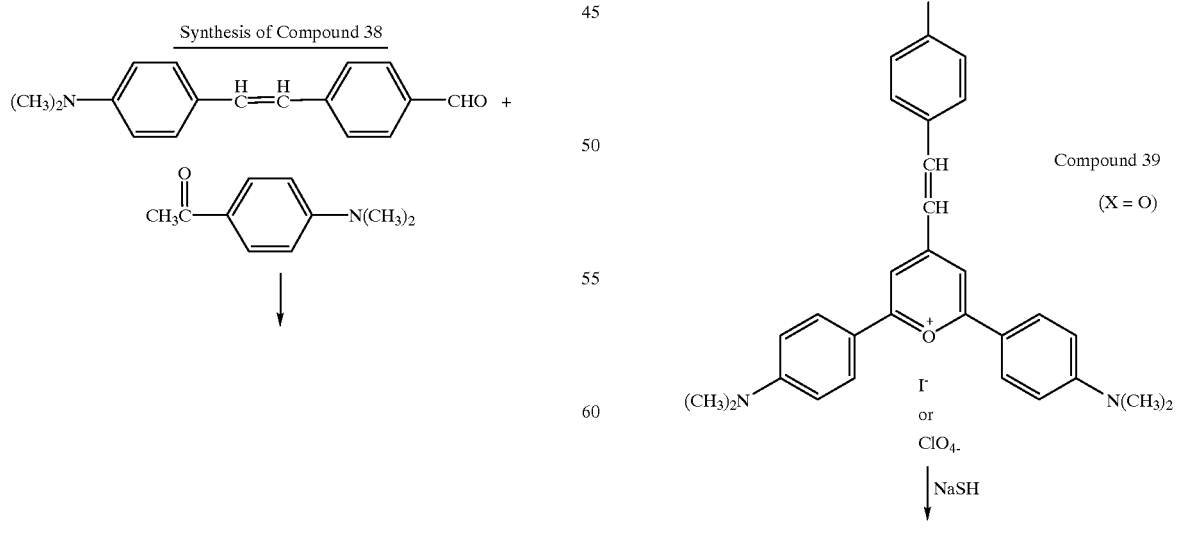

-continued

Compound 39 (X = S)

The compound 40 was obtained in the same manner as said for the compound 36 with the exception that the material

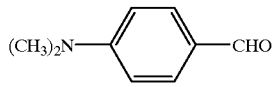

was replaced with

The compound 41 was obtained in the same manner as said for the compound 37 with the exception that the material

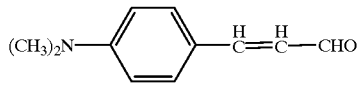

was replaced with

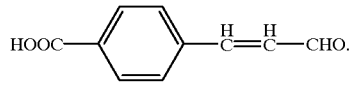

The compound 42 was obtained in the same manner as said for the compound 38 with the exception that the material

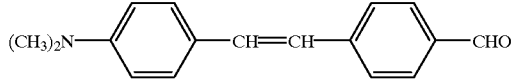

was replaced with

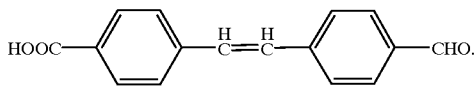

The compound 43 was obtained in the same manner as said for the compound 39 with the exception that the material

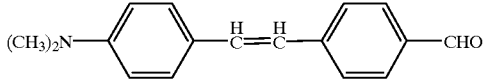

was replaced with

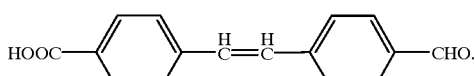

Synthesis of Compound 44

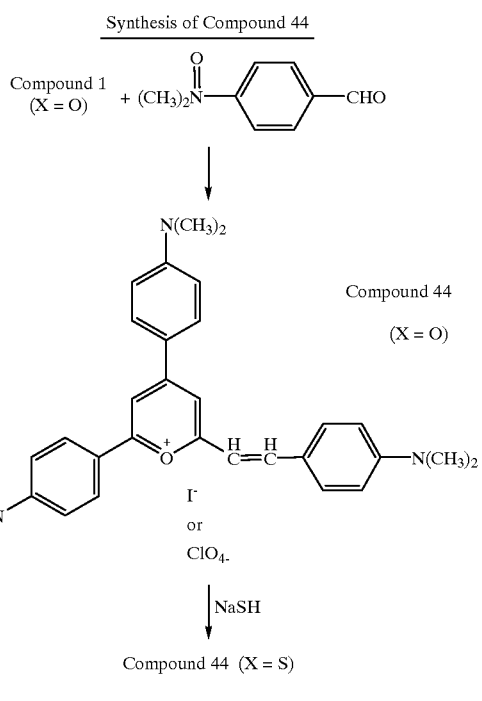

Synthesis of Compound 45

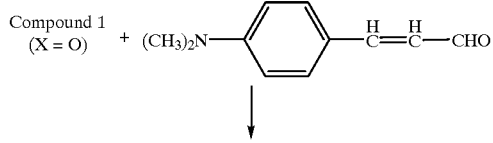

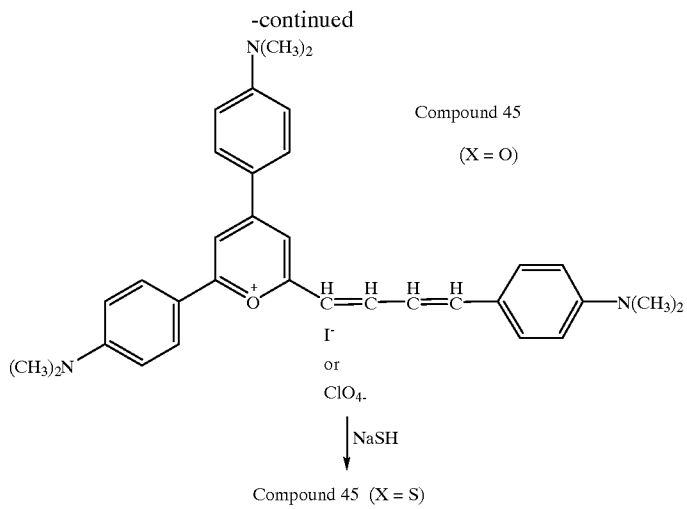

-continued

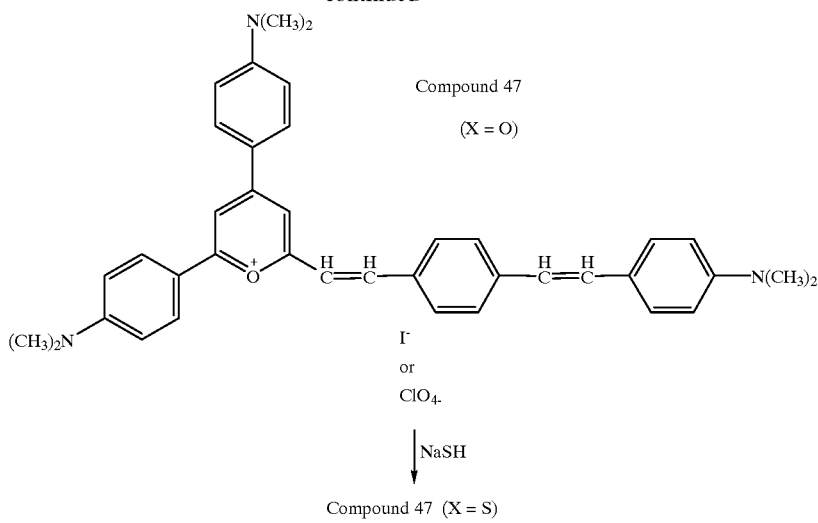

Compound 47
(X = O)

I⁻
or
ClO₄⁻

↓ NaSH

Compound 47 (X = S)

The compound 48 was obtained in the same manner as said for the compound 44 with the exception that the material

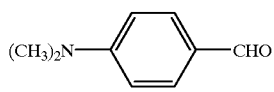

was replaced with

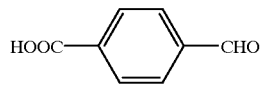

The compound 49 was obtained in the same manner as said for the compound 45 with the exception that the material

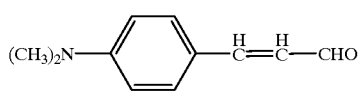

was replaced with

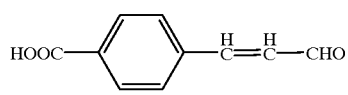

The compound 50 was obtained in the same manner as said for the compound 46 with the exception that the material

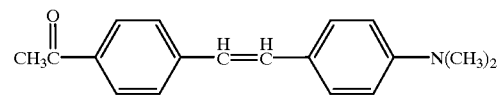

was replaced with

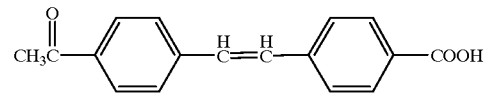

The compound 51 was obtained in the same manner as said for the compound 47 with the exception that the material

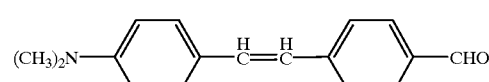

was replaced with

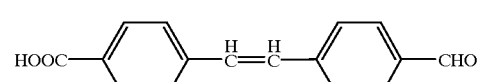

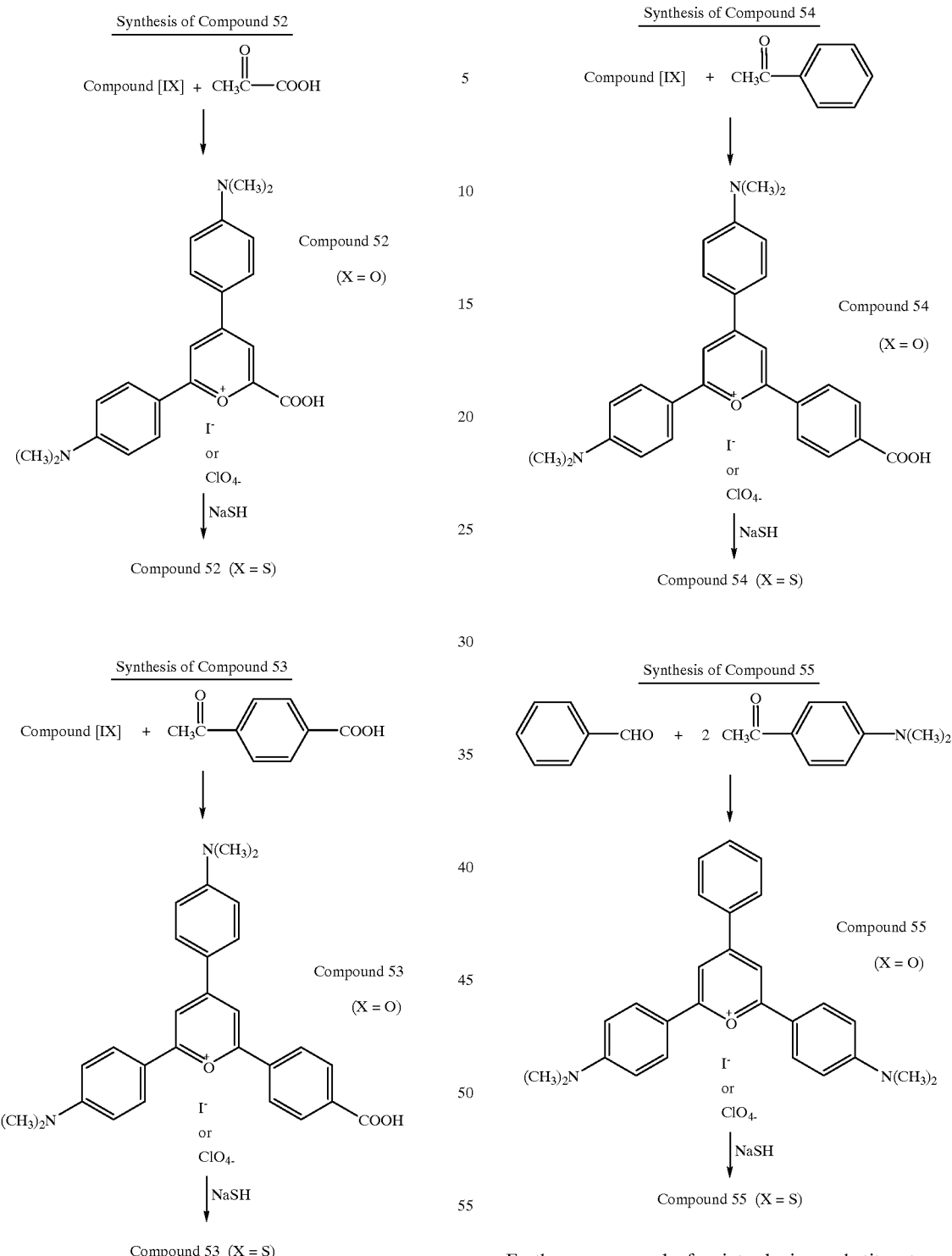
Further, compounds for introducing substituents were modified in several ways to obtain the compounds shown in Table 2.

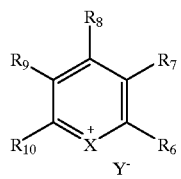

| Compound No. | X | Y | $R_i$ | L | A |
|---|---|---|---|---|---|
| 56 | O | $ClO_4$ or I | $R_6 = CH_3$<br>$R_7 = H$<br>$R_8 = \Phi$<br>$R_9 = H$<br>$R_{10} = A$ | | $\Phi$ |
| 57 | S | $ClO_4$ or I | $R_6 = CH_3$<br>$R_7 = H$<br>$R_8 = \Phi$<br>$R_9 = H$<br>$R_{10} = A$ | | $\Phi$ |
| 58 | O | $ClO_4$ or I | $R_6 = \Phi$<br>$R_7 = H$<br>$R_8 = A$<br>$R_9 = H$<br>$R_{10} = \Phi$ | | $\Phi$ |
| 59 | S | $ClO_4$ or I | $R_6 = \Phi$<br>$R_7 = H$<br>$R_8 = A$<br>$R_9 = H$<br>$R_{10} = \Phi$ | | $\Phi$ |
| 60 | O | $ClO_4$ or I | $R_6 = \Phi$<br>$R_7 = H$<br>$R_8 = L\text{---}A$<br>$R_9 = H$<br>$R_{10} = \Phi$ | general formula [II]<br>n = 0<br>Z = H | $\Phi$ |
| 61 | S | $ClO_4$ or I | $R_6 = \Phi$<br>$R_7 = H$<br>$R_8 = L\text{---}A$<br>$R_9 = H$<br>$R_{10} = \Phi$ | general formula [II]<br>n = 0<br>Z = H | $\Phi$ |
| 62 | O | $ClO_4$ or I | $R_6 = \Phi$<br>$R_7 = H$<br>$R_8 = \Phi$<br>$R_9 = H$<br>$R_{10} = L\text{---}A$ | general formula [II]<br>n = 0<br>Z = H | $\Phi$ |
| 63 | S | $ClO_4$ or I | $R_6 = \Phi$<br>$R_7 = H$<br>$R_8 = \Phi$<br>$R_9 = H$<br>$R_{10} = L\text{---}A$ | general formula [II]<br>n = 0<br>Z = H | $\Phi$ |
| 64 | O | $ClO_4$ or I | $R_6 = \Phi$<br>$R_7 = H$<br>$R_8 = L\text{---}A$<br>$R_9 = H$<br>$R_{10} = \Phi$ | general formula [II]<br>n = 1<br>Z = H | $\Phi$ |
| 65 | S | $ClO_4$ or I | $R_6 = \Phi$<br>$R_7 = H$<br>$R_8 = L\text{---}A$<br>$R_9 = H$<br>$R_{10} = \Phi$ | general formula [II]<br>n = 1<br>Z = H | $\Phi$ |
| 66 | O | $ClO_4$ or I | $R_6 = \Phi$<br>$R_7 = H$<br>$R_8 = L\text{---}A$<br>$R_9 = H$<br>$R_{10} = \Phi$ | general formula [II]<br>n = 1<br>Z =<br>$(-)CH{=}CH\text{-}\Phi\text{-}N(CH_3)_2$ | $\Phi$ |
| 67 | S | $ClO_4$ or I | $R_6 = \Phi$<br>$R_7 = H$<br>$R_8 = L\text{---}A$<br>$R_9 = H$<br>$R_{10} = \Phi$ | general formula [II]<br>n = 1<br>Z =<br>$(-)CH{=}CH\text{-}\Phi\text{-}N(CH_3)_2$ | $\Phi$ |
| 68 | O | $ClO_4$ or I | $R_6 = \Phi$<br>$R_7 = H$<br>$R_8 = L\text{---}A$<br>$R_9 = H$<br>$R_{10} = \Phi$ | general formula [III]<br>n = 1 | $\Phi$ |
| 69 | S | $ClO_4$ or I | $R_6 = \Phi$<br>$R_7 = H$ | general formula [III]<br>n = 1 | |

-continued

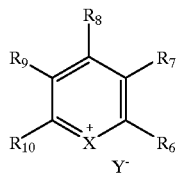

| Compound No. | X | Y | $R_i$ | L | A |
|---|---|---|---|---|---|
| 70 | O | $ClO_4$ or I | $R_6 = \Phi$<br>$R_7 = H$<br>$R_8 = L\text{—}A$<br>$R_9 = H$<br>$R_{10} = \Phi$ | general formula [IV] | $\Phi$ |
| 71 | S | $ClO_4$ or I | $R_6 = \Phi$<br>$R_7 = H$<br>$R_8 = L\text{—}A$<br>$R_9 = H$<br>$R_{10} = \Phi$ | general formula [IV] | $\Phi$ |
| 72 | O | $ClO_4$ or I | $R_6 = \Phi$<br>$R_7 = H$<br>$R_8 = \Phi$<br>$R_9 = H$<br>$R_{10} = L\text{—}A$ | general formula [IV] | $\Phi$ |
| 73 | S | $ClO_4$ or I | $R_6 = \Phi$<br>$R_7 = H$<br>$R_8 = \Phi$<br>$R_9 = H$<br>$R_{10} = L\text{—}A$ | general formula [IV] | $\Phi$ |
| 74 | O | $ClO_4$ or I | $R_6 = \Phi$<br>$R_7 = H$<br>$R_8 = \Phi$<br>$R_9 = H$<br>$R_{10} = L\text{—}A$ | general formula [V] | 4-Φ, 2,6-Φ pyran-2-ylidene methyl |
| 75 | S | $ClO_4$ or I | $R_6 = \Phi$<br>$R_7 = H$<br>$R_8 = \Phi$<br>$R_9 = H$<br>$R_{10} = L\text{—}A$ | general formula [V] | 4-Φ, 2,6-Φ thiopyran-2-ylidene methyl |
| 76 | O | $ClO_4$ or I | $R_6 = \Phi$<br>$R_7 = H$<br>$R_8 = \Phi$<br>$R_9 = H$<br>$R_{10} = L\text{—}A$ | general formula [V] | 4-Φ, 2,6-Φ thiopyran-2-ylidene methyl |
| 77 | O | $ClO_4$ or I | $R_6 = \Phi$<br>$R_7 = H$<br>$R_8 = \Phi$<br>$R_9 = H$<br>$R_{10} = L\text{—}A$ | general formula [VI] | 4-Φ, 2,6-Φ pyran-2-ylidene methyl |
| 78 | S | $ClO_4$ or I | $R_6 = \Phi$<br>$R_7 = H$<br>$R_8 = \Phi$<br>$R_9 = H$<br>$R_{10} = L\text{—}A$ | general formula [VI] | 4-Φ, 2,6-Φ thiopyran-2-ylidene methyl |

-continued

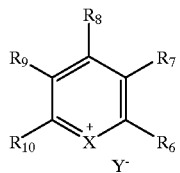

| Compound No. | X | Y | $R_i$ | L | A |
|---|---|---|---|---|---|
| 79 | O | $ClO_4$ or I | $R_6 = \Phi$<br>$R_7 = H$<br>$R_8 = \Phi$<br>$R_9 = H$<br>$R_{10} = L-A$ | general formula [VI] | (-)CH=⟨S,Φ,Φ⟩ |
| 80 | O | $ClO_4$ or I | $R_6 = \Phi$<br>$R_7 = H$<br>$R_8 = \Phi$<br>$R_9 = H$<br>$R_{10} = L-A$ | general formula [II]<br>n = 0<br>Z = H | azulenyl-CH₃, H₃C |
| 81 | S | $ClO_4$ or I | $R_6 = \Phi$<br>$R_7 = H$<br>$R_8 = \Phi$<br>$R_9 = H$<br>$R_{10} = L-A$ | general formula [II]<br>n = 0<br>Z = H | azulenyl-CH₃, H₃C |
| 82 | O | $ClO_4$ or I | $R_6 = \Phi$<br>$R_7 = H$<br>$R_8 = \Phi$<br>$R_9 = H$<br>$R_{10} = L-A$ | general formula [II]<br>n = 0<br>Z = H | (-)CH=⟨O,Φ,Φ⟩ |
| 83 | S | $ClO_4$ or I | $R_6 = \Phi$<br>$R_7 = H$<br>$R_8 = \Phi$<br>$R_9 = H$<br>$R_{10} = L-A$ | general formula [II]<br>n = 0<br>Z = H | (-)CH=⟨S,Φ,Φ⟩ |
| 84 | O | $ClO_4$ or I | $R_6 = \Phi$<br>$R_7 = H$<br>$R_8 = \Phi$<br>$R_9 = H$<br>$R_{10} = L-A$ | general formula [II]<br>n = 0<br>Z = H | (-)CH=⟨O,Φ,Φ⟩ |
| 85 | O | $ClO_4$ or I | $R_6 = \Phi$<br>$R_7 = H$<br>$R_8 = L-A$<br>$R_9 = H$<br>$R_{10} = \Phi$ | general formula [II]<br>n = 0<br>Z = H | (-)CH=⟨O,Φ,Φ⟩ |

-continued

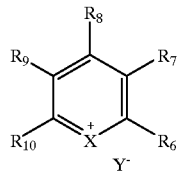

| Compound No. | X | Y | $R_i$ | L | A |
|---|---|---|---|---|---|
| 86 | S | $ClO_4$ or I | $R_6 = \Phi$<br>$R_7 = H$<br>$R_8 = L-A$<br>$R_9 = H$<br>$R_{10} = \Phi$ | general formula [II]<br>n = 0<br>Z = H | (-)CH=⟨pyran-S with 2Φ⟩ |
| 87 | O | $ClO_4$ or I | $R_6 = \Phi$<br>$R_7 = H$<br>$R_8 = L-A$<br>$R_9 = H$<br>$R_{10} = \Phi$ | general formula [II]<br>n = 0<br>Z = H | (-)CH=⟨pyran-S with 2Φ⟩ |
| 88 | O or S | $ClO_4$ or I | $R_6 = \Phi$<br>$R_7 = H$<br>$R_8 = A$<br>$R_9 = H$<br>$R_{10} = \Phi$ | | —$CH_3$ |
| 89 | same as the above | same as the above | same as the above | | $\Phi$-COOH |
| 90 | O or S | $ClO_4$ or I | $R_6 = \Phi$<br>$R_7 = H$<br>$R_8 = L-A$<br>$R_9 = H$<br>$R_{10} = \Phi$ | general formula [II]<br>n = 0<br>Z = H | $\Phi$-COOH |
| 91 | same as the above | same as the above | same as the above | general formula [II]<br>n = 1<br>Z = H | $\Phi$-COOH |
| 92 | O or S | $ClO_4$ or I | $R_6 = \Phi$<br>$R_7 = H$<br>$R_8 = L-A$<br>$R_9 = H$<br>$R_{10} = \Phi$ | general formula [III]<br>n = 1 | $\Phi$-COOH |
| 93 | same as the above | same as the above | same as the above | general formula [IV] | $\Phi$-COOH |
| 94 | O or S | $ClO_4$ or I | $R_6 = L-A$<br>$R_7 = H$<br>$R_8 = \Phi$<br>$R_9 = H$<br>$R_{10} = \Phi$ | general formula [II]<br>n = 1<br>Z = H | $\Phi$ |
| 95 | same above above | same as the above | same as the above | general formula [III]<br>n = 1 | $\Phi$ |
| 96 | O or S | $ClO_4$ or I | $R_6 = L-A$<br>$R_7 = H$<br>$R_8 = \Phi$<br>$R_9 = H$<br>$R_{10} = \Phi$ | general formula [II]<br>n = 0<br>Z = H | $\Phi$-COOH |
| 97 | same as the above | same as the above | same as the above | general formula [II]<br>n = 1<br>Z = H | $\Phi$-COOH |
| 98 | same as the above | same as the above | same as the above | general formula [III]<br>n = 1 | $\Phi$-COOH |
| 99 | O or S | $ClO_4$ or I | $R_6 = L-A$<br>$R_7 = H$<br>$R_8 = \Phi$<br>$R_9 = H$<br>$R_{10} = \Phi\text{-}N(CH_3)_2$ | general formula [IV] | $\Phi$-COOH |
| 100 | same as the above | same as the above | $R_6 = A$<br>$R_7 = H$<br>$R_8 = \Phi$<br>$R_9 = H$<br>$R_{10} = \Phi$ | | —COOH |

-continued

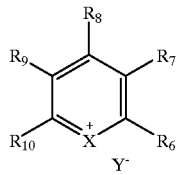

| Compound No. | X | Y | $R_i$ | L | A |
|---|---|---|---|---|---|
| 101 | same as the above | same as the above | same as the above | | Φ-COOH |

Example 1 (Detection of DNA Hybrid by Two Pyrylium Dyes)

[1] Synthesis of 2-methyl-4,6-bis-(4-N,N-dimethylaminophenyl)pyrylium iodide (Compound a)

As described in Reference Example 1, acetic anhydride (100 ml) and concentrated sulphuric acid (30 ml) were mixed by cooling, and the resultant mixture solution was heated in a water bath with the temperature at 80° C. maintained. To the mixture, acetic anhydride (20 ml) and p-dimethylaminoacetophenone (30 ml) were further added at room temperature. The obtained mixture was heated to 45° C. and stirred for 24 hours. To the reacted solution, ethanol of an equivalent volume was added, and the mixture solution was cooled, followed by addition of potassium iodide solution. The precipitated crude crystal was collected by filtration, and recrystallized with a mixture solvent of ethanol/ether (volume ratio: 1/4) to obtain 2-methyl-4,6-bis-(4-N,N-dimethylaminophenyl)pyrylium iodide (Compound a).

[2] Synthesis of 4-methyl-2,6-diphenylpyrylium perchlorate

According to the method of A. T.Balaban et al. (Tetrahedron, 20, 119, 1964), 4-methyl-2,6-diphenylpyrylium perchlorate (Compound b) was synthesized.

[3] Synthesis of Oligonucleotide

A target DNA of 20-mer oligonucleotide having a base sequence which is partly complementary with M13mp18DNA (single stranded) was synthesized by 381A DNA synthesizer (manufactured by ABI K.K.). Dimethoxytrityl group at 5' terminal was excluded by the automatic synthesizer. The base sequence of the target DNA is as follows:

5'-GTTGTAAAACGACGGCCAGT-3' (Sequence No.:1)

[4] Formation of Hybrid of Probe and M13mp18DNA

Oligonucleotide probe synthesized in the above [3] step (0.2 microM) and M13mp18DNA (manufactured by Takara Syuzo K.K.) (0.2 microM) were heated in a lmM phosphate buffer (pH7.0)/145 mM NaCl/5 mM KCl at 80° C., and gradually cooled to room temperature to prepare hybrid of the probe and the target DNA.

[5] Properties of Two Kinds of Dyes

Each of the compounds a and b was added to a DNA solution to study an interaction of each compound and nucleic acids. The compound a alone was not fluorescent in solution (absorption peak: 540 nm), but was excited to emit fluorescence at 580 nm and strongly fluorescent at 640 nm in DNA solution. Also, the absorption peak of the compound a was shifted by ca. 40 nm to longer wave length by adding DNA, showing that the compound a was a fluorescent intercalator. On the other hand, the compound b is strongly fluorescent in free condition, but not fluorescent in the presence of DNA.

[6] Detection of Hybrid Through Charge Transfer Utilizing The Two Kinds of Pyrylium Dyes To the hybrid of the probe prepared in the above [4] step and M13mp18, the compound a was added to reach to a final concentration of 5 microm, followed by addition of the compound b in varied concentrations. To each solution, a visible light at 580 nm which was an absorption wave length of the compound a was irradiated, and the emitted fluorescence was measured by IMUC-7000 (manufactured by Otsuka Denshi K.K.). The fluorescence at 640 nm observed before addition of the compound b reduced with addition of compound b, and a new fluorescence appeared at 450 nm instead. The appearance of fluorescence at 450 nm is considered to be caused by the fact that charge was transferred through a double helix structure between the compound a and the compound b inserted in the hybrid. The strength of fluorescence at 450 nm was found to be maximum by adjusting the compound b to 5 microm.

Example 2 (Detection of Mismatch)

A hybrid of probe and target oligonucleotide was prepared in the same manner as in Example 1 with the exception that an oligonucleotide of the following base sequence was utilized as a probe;

5'-GTTGTAAAAGGACGGCCAGT-3' (Sequence No.:2)

This base sequence is the same as in Example 1 with the exception that its base C of the 10th from the 5' terminal was replaced with G, and was designed to mismatch with M13mp18DNA.

To the hybrid, two kinds of pyrylium compounds were added in the same manner as said for the Example 1. Next, lights at 580 nm were irradiated to measure strength of the resultant fluorescence at 450 nm and 640 nm. Unlikely to the Example 1, either the compound a or the compound b was not found to change in fluorescence strength. This result was considered to be caused by the fact that interaction was not occurred between the dyes combined to a mismatched hybrid.

Example 3 (Detection of DNA Hybrid with Two Kinds of Pyrylium Dyes)

Hybrid of probe and target DNA was prepared in the same manner as in Example 1. To the hybrid, the compound a was added, and 2,6-bis-(N,N-dimethylaminophenyl)-4-phenylpyrylium iodide (Compound c) was further added.

An interaction of the compound c and DNA was studied in advance. The compound c was found to absorb at ca. 600 nm and to shift its absorption spectrum to 640 nm with the addition of DNA. The compound c was therefore considered to be intercalator, but its fluorescence strength was small even in a DNA solution.

To the hybrid of probe and target DNA, the pyrilium compound a was added to reach to a final concentration of 5 μM and compound c was added in varied concentrations, and a light at 580 nm was irradiated to excite the compound a. The strong fluorescence (640 nm) of the compound a observed in the presence of DNA and in the absence of the compound c is reduced with addition of compound c, and a new fluorescence at 720 nm was observed. This phenomena was considered to be caused by an energy transfer from the compound a to the compound c. By varying the amount of the compound c, reduction of the donor fluorescence and elevation of the acceptor fluorescence were found to be maximum by utilizing the same molecular amount of the compound a as that of the compound c.

Example 4 (Detection of Hybrid with Labelled Antibody by Charge Transfer)

[1] Preparation of Labelled Antibody (1) Synthesis of 4-methyl-2,6-diphenylpyrylium perchlorate According to the method of A. T.Balaban et al. (Tetrahedron, 20, 119, 1964), 4-methyl-2,6-diphenylpyrylium perchlorate (Compound b) was synthesized.

(2) Labelling of Antibody

A mixture solution of the compound b (4.3 g), carboxybenzaldehyde (2 g), 70% perchloric acid (one drop), and acetic acid (10 ml) was refluxed for one hour. The precipitant was collected and recrystallized with a mixture solvent of ethanol and ether to obtain 4-(4-carboxystyryl)-2,6-diphenylpyrylium perchlorate (compound d).

The compound d (170 mg) was dissolved in dried DMF (5 ml), and dried pyridine (50 microl) was added. After DSC (disucciimidylcarbonate) (128 mg) was further added, the mixture solution was stirred in the darkness at room temperature for 20 hours. To the reacted solution, diethyl ether (150 ml) was added. The precipitant was collected, washed with diethyl ether, and dried. The obtained active ester (compound e) was made to react with amino group of antibody to prepare labelled antibody.

[2] Detection with FITC-labelled Secondary Antibody

The primary antibody prepared in the above step [2] was made to react with antigen, and further made to react with a secondary antibody of FITC-labelled anti-mouse IgG antibody (manufactured by Sigma Co.).

To the resultant sample, a visible light at 480 nm was irradiated, and fluorescence was measured by IMUC-7000 (manufactured by Otsuka Denshi K.K.). As the result, fluorescence of FITC observed at 520 nm before the reaction of the labelled antibody is reduced, and a new fluorescence was observed at 450 nm instead. This is considered to be caused by the reaction of the primary and the secondary antibody and charge transfer between the compound b on the labelled antibody and FITC.

Example 5

[1] The Compound a Synthesized in the Example 1 was Utilized as Pyrylium Compound.

[2] Preparation of 20-mer Oligonucleotide Combined with TEMPO (4-hydroxy-2,2,6,6-tetramethylpiperidine) of Spin Labelling Agent (1) Synthesis of 4-aminohexylamino-2,2,6,6-tetramethylpiperidine-N-oxyl (4-aminohexylamino-TEMPO)

4-oxo-TEMPO (0.5 mmole) and hexamethylenediamine dichloride (5 mmole) were dissolved in methanol (30 ml). To the mixture solution, sodium cyanoborohydride (0.4 mmole) and molecular sieve 3A were added, followed by stirring at room temperature for 24 hours. Next, the reacted solution was filtered by a glass filter to remove the molecular sieve, and evaporated under reduced pressure to remove the solvent. To the residue, 1N chloric acid (30 ml) was added, and the solution was extracted with chloroform. The chloroform layer was washed with water and evaporated under reduced pressure. The residue was filtered with water, and the filtered solution was further evaporated under reduced pressure to obtain a red oil substance.

(2) Oligonucleotide

The oligonucleotide synthesized in the Example 1 was utilized.

(3) Synthesis of Spin-labelled Oligonucleotide Probe

The oligonucleotide synthesized in the above step (2) (1 micromole) was transferred to a gas tight syringe under the condition that the oligonucleotide was combined on a CPG support. The following reactions were made in the syringe. To the CPG support, carbonyl-N,N'-diimidazole (CDI) (50 mg) dissolved in dioxane (1 ml) was added, followed by leaving at room temperature for one hour. The resultant mixture was washed with dioxane and dried under reduced pressure. Next, 4-aminohexylamino-TEMPO in DMSO solution (0.2M 0.4 ml) was added, and the resultant mixture solution was left at 55° C. for 24 hours. The obtained mixture was washed with DMSO, dioxane and methanol in this order and dried under reduced pressure.

Spin-labelled oligonucleotide was then cleaved with concentrated ammonia water according to a general method to remove protection, and purified by RPLC.

[3] Formation of Hybrid of TEMPO Probe and M13mp18DNA

The oligonucleotide probe having TEMPO introduced according to the above step [2] (0.2 microM) and M13mp18DNA (manufactured by Takara Syuzo) (0.2 microM) were heated in 1 mM phosphate buffer (pH7.0)/145 mM NaCl/5 mM KCl at 80° C., and gradually cooled to room temperature to prepare a hybrid of probe and target DNA. Next, the compound a was added to the reacted solution to obtain a final concentration of 5 microM, and ESR spectrum was measured as follows. Separately, the same manipulations as said were conducted with no M13mp18DNA utilized to prepare a sample (probe alone) for ESR spectrum measurement.

[4] Measurement of ESR Spectrum

ESR measurement was sweeped at 20 minutes/sample for 100 minutes. Changes in the strength ratio and in the width of line were chased with time. ESR manufactured by Nihon Denshi K.K. was utilized. Flat cell of artificial quarz was utilized for measurement.

ESR and a light irradiation machine were adjusted as follows;

| frequency | 9.42 GHz |
|---|---|
| Modulation | 100 kHz 0.1 mT |
| Field | 335 mT |
| Time Constant | 0.3 sec |
| Power | 10 mW |
| Sweep Time | 8 min |
| Receiver Gain | 1.25 × 1000 |

Light Irradiation Machine

Monochrometer 580 nm

Power supply 88.5V–89V/22A

Changes in the strength ratio and the width of line of ESR signal with time were shown in FIG. 3. As shown in the FIG. 3, no change was observed in the strength ratio and the width by irradiation for a probe alone. Also, no change was observed by no irradiation even for the compound a/probe/M13mp18.

When a light was irradiated to the compound a/probe/M13mp18DNA at 580 nm which was a maximum absorption for the combining of the compound a/DNA, ESR was reduced in the strength ratio with time. Since no change was observed in the width of line, change in the ESR strength was considered not to be caused by chemical change. Therefore, spin of TEMPO was confirmed to disappear due to charge transfer from the compound a through a double helix structure of probe and M13mp18DNA to TEMPO combined with the probe. Hybrid of probe and target DNA was thus detected without B/F separation.

Example 6

Detection of Change in Nucleic Acid Base by HPLC

[1] Preparation of Probe Combined with The Compound a at 3' Terminal (1) Esterification of the compound a A mixture solution of the compound a (4.3 g), carboxybenzaldehyde (2 g), 70% perchloric acid (one drop), and acetic acid (10 ml) was refluxed for one hour. The precipitant was collected and recrystallized with a mixture solvent of ethanol/ether to obtain 2-(4-carboxystyryl)-4,6-bis-(4-N,N-dimethylaminophenyl)pyrylium perchlorate (Compound f).

The compound f (170 mg) was dissolved in dried DMF (5 ml), followed by addition of dried pyridine (50 microl) and DSC (disucciimidylcarbonate) (128 mg). The mixture solution was then stirred at room temperature in the darkness for 20 hours. To the reacted mixture solution, diethyl ether (150 ml) was added. The precipitant was collected, washed with diethyl ether, and dried. The obtained active ester (Compound g) was utilized to react with nucleic acids.

(2) Synthesis of Oligonucleotide

Oligonucleotide having the same sequence as in Example 1 was synthesized by a DNA synthesizer. The oligonucleotide was provided with thiol linker at 5' terminal and amino linker at 3' terminal for combining with an electron donor or acceptor, as well as an effective sequence. For linker combining, reagents of 5' thiol modifier C6 and amino modifier dT (manufactured by Gren Research Co.) were utilized respectively. Cleavage from CPG support, removal of protection, and purification by HPLC were also conducted according to protocols designated by Gren Research Co.

(3) Reaction of Compound g and Oligonucleotide

To phosphate buffer (0.8 ml) (0.1M pH=7.0) containing the oligonucleotide prepared in the above step (2) ($10D_{260}$), acetonitrile solution (0.2 ml) containing the compound g (1 mg) was added, followed by leaving at 40° C. for 24 hours. The reacted solution was purified through NAP column (manufactured by Pharmacia Co.), and further purified by HPLC to obtain probe having the compound a at 3' terminal combined (compound h).

[2] Absorption Spectrum of Hybrid

Next, an absorption spectrum was measured for the reacted solution. The absorption maximum of 3' terminal labelled probe (compound h) alone was observed at 540 nm at which the absorption maximum of the compound a was observed. On the other hand, the absorption maximum of hybrid of probe and M13mp18 was observed at 580 nm which was shifted from that for the compound a. This phenomenon revealed that the compound a functioned as intercalator even for hybrid.

[3] Irradiation to Hybrid

To the hybrid, a visible light at 580 nm was irradiated for excitation from a xenon lamp equipped with a band pass filter. Irradiation time was made to vary from 5 to 20 minutes at an interval of five minutes.

[4] Nucleoside Analysis by HPLC

After irradiation, the sample was made to react with Exonuclease III (manufactured by Takara Syuzo K.K.) and alkali phosphatase (manufactured by Takara Syuzo K.K.) at 37° C. to completely cleave a double stranded part of hybrid consisting of probe and target DNA and to form nucleoside.

Next, the nucleoside was separated by HPLC. Specifically, the nucleoside was eluted with methanol containing 10 mM triethylamineacetate solution on gradient (10–40%) through a reverse phase column (Wacosil®, manufactured by Wako Zyunyaku K.K.).

All of four deoxynucleosides (dA, dG, dC, dT) were eluted within a retention time of 10 minutes. Other than these, unknown peaks were detected which had absorption maximums at 250 nm in 13 minutes and 280 nm in 19 minutes. The amount of the substance eluted was increased in proportion to that of irradiation by the time ten minutes passed, and then maintained constant.

The same experiment was conducted for hybrid of non-labelled probe and target DNA for control. Irradiation time of the xenon lamp was made to vary from 5 to 20 minutes and a double stranded part of hybrid was completely cleaved to form nucleoside, but any peaks were not observed except that of dA, dG, dC, dT. Comparison of composition of nucleosides for non-labelled probe with that for labelled probe suggested that the two unknown nucleosides were nucleosides modified by change of G-C base pairs.

Also, these two peaks were not found even for labelled probe and for a hybrid to which irradiation was not conducted.

Example 7

Detection of Hybrid by Charge Transfer with Labelled Antibody

[1] Preparation of Labelled Antibody (1) Preparation of antibody

Antibody was prepared by utilizing the two modified nucleosides obtained in the example 6 as antigens and mouse according to a general method.

(2) Synthesis of 4-methyl-2,6-diphenylpyrylium perchlorate was synthesized in the same manner as in Example 4.

(3) Labelled antibody was prepared in the same manner as in Example 4.

[2] Detection of Hybrid

To hybrid of M13mp18 and probe (the compound h) combined with the compound a at its 3' terminal and prepared in the example 6, a visible light at 580 nm was irradiated for 10 minutes. To the resultant hybrid, the labelled antibody prepared in the above step [1] was reacted.

To the reacted sample, a visible light at 580 nm was irradiated again, and the resulting fluorescence was measured by IMUC-7000 (manufactured by Otsuka Denshi K.K.). As the result, the fluorescence at 640 nm observed before reaction with the labelled antibody disappeared, and fluorescence at 450 nm was newly appeared. This phenomenon reveals that charge was transferred between the compound a inserted into the hybrid and the compound b on the labelled antibody.

Example 8

Detection of DNA Hybrid of Probe Combined with two Pyrylium Dyes

[1] Preparation of Probe Combined with the Compound a at 3' Terminal and the Compound b at 5' Terminal (1) Formation of styryl from the compound b The compound b was reacted with 4-aminobenzaldehyde in the same manner as that for the compound f to synthesize 4-(4-aminostyryl)-2,6-diphenylpyrylium perchlorate (compound i).

Anhydrous maleic acid (196 mg) was dissolved in chloroform (10 ml). To the solution, a chloroform solution (2 ml) of the compound i (450 mg) was added, followed by stirring at room temperature for one hour. The mixture was then cooled to 15° C., and the precipitate was collected. The resultant maleic acid-added intermediate (Compound j) was utilized for the following reaction.

To acetic anhydride (10 ml), sodium acetate (anhydrous) (1 g) was added for dissolution. To the solution, the compound j (250 mg) was added, followed by vigorous stirring. The resultant solution was further stirred at 90° C. for 30 minutes, cooled to room temperature, and poured into ice water (20 ml). The precipitant was collected, washed with water three times, dried, and recrystallized with ethanol to obtain 4-(4-maleimidylstyryl)-2,6-diphenylpyrylium perchlorate (Compound k).

(2) Introduction of the compound i to 5' terminal of oligonucleotide

To phosphate buffer (0.8 ml) (0.1M pH=7.0) containing oligonucleotide combined with the compound a at its 3' terminal (the compound h), acetonitrile solution (0.2 ml) of the compound k (1 mg) was added. The mixture was then left at 40° C. for 24 hours. The reacted mixture was purified through NAP column (manufactured by Pharmacia Co.) to obtain a crude product, and further purified by HPLC. Oligonucleotide probe labelled with pyrylium dyes at both of the terminals (Compound 1) was thus prepared.

[3] Preparation of Probe Combined with the Compound k at 5' Terminal (for Control)

Probe labelled with the compound b at 5' terminal was prepared (Compound m) by utilizing oligonucleotide not combined with the compound a at 3' terminal in the same manner as that for the probe labelled at both of the terminals.

[4] Formation of Hybrid of the Probe Labelled at Both of the Terminals and M13mp18DNA Oligonucleotide probe combined with electron donor and electron acceptor at both of the terminals and prepared according to the above step [2] and M13mp18DNA (0.2 microM) were heated in 1 mM phosphate buffer (pH7.0)/145 mM NaCl/5 mM KCl at 80° C., and gradually cooled to room temperature to prepare hybrid of probe and target DNA.

[5] Measurement of Fluorescence Spectrum

Next, to the reacted solution, a visible light at 580 nm at which the absorption maximum was obtained by combining the compound a with DNA was irradiated from a xenon lamp equipped with a band pass filter. Fluorescence was measured by IMUC-7000 (manufactured by Otsuka Denshi K.K.).

Fluorescence was not observed in any wavelength for the hybrid of the compound m and M13mp18. On the other hand, fluorescence at 640 nm derived from the compound a disappeared, and fluorescence at 450 nm was newly appeared for hybrid of the compound 1 and M13mp18. This is considered to be caused by charge transfer from the compound a to the compound b.

FIG. 4 shows the spectrum.

Example 9

Detection of DNA Hybrid of Probe Combined with Pyrylium Compound of One Kind

Hybrid of probe combined with the compound a at 3' terminal and M13mp18DNA was prepared in the same manner as in Example 6. To the hybrid, compound c which was used in Example 3 was added to obtain a final concentration of 5 microM.

When a light at 580 nm which excites the compound a was irradiated to hybrid of probe and target DNA, fluorescence at 640 nm due to an interaction of the compound a and DNA was disappeared, and fluorescence at 720 nm was newly appeared. This phenomenon is considered to be caused by energy transfer from the compound a to the compound c.

Fluorescence strength at 720 nm was larger than that in Example 3. This phenomena means that the functionalization of compound a to probe made possible an efficient energy transfer.

According to a method for detection in the present invention, a target substance can be detected at high accuracy. For example, when a target substance is in the form of hybrid prepared by hybridization with probe, it can be advantageously detected without B/F separation. Therefore, many manipulations are not required for the present invention, and examples of them include exclusion of excessive probes which were essential for the conventional methods, complicated treatments to exclude non-specific absorption, and considerations on experimental conditions. Further, only hybrid forming an accurate double helix structure can be detected even if a reaction system includes mismatch, by selecting reagents to detect signal changes from correct hybrid.

When pyrylium compounds are utilized as electron donor according to the invention, S/N ratio for detection can be elevated by utilizing the compounds which hardly emit fluorescence under free condition, and whose fluorescence properties are largely varied at the time of combining with a double helix structure of nucleic acids. Pyrylium compounds are inserted into a double helix structure at higher specificity compared to other intercalators of condensed ring, and are hardly inserted into a double chain structure in single stranded DNA. Therefore, signals from pseudo-hybrid partly having a double chain structure can be successfully excluded by utilizing pyrylium compounds for at least one of the two reagents.

Also, when reagents are combined with probe, only hybrid forming a correct double helix structure can be detected even if a reaction system includes mismatch, by selecting reagents so that only signal changes from a correct hybrid may be measured.

Pyrylium compounds utilized as electron donor or energy donor have additional advantages that they are not fluorescent or are weak-fluorescent when combined with probe forming single stranded or when utilized in free condition, leading to higher sensitivity for detection than the conventionally-utilized reagents.

---

Sequence Table sequence No.: 1 length: 20
type: nucleic acid
strandedness: single
topology: linear
kind: other nucleic acid, synthetic DNA
sequence characteristics: probe sequence for detection -continued Sequence Table of M13mp18DNA
sequence
    GTTGTAAAAC GACGGCCAGT 20
Sequence No.: 2 length: 20
type: nucleic acid
strandedness: single
topology: linear
kind: other nucleic acid, synthetic DNA
sequence characteristics: probe sequence for mismatch
with M13mp18DNA
sequence
    GTTGTAAAAG GACGGCCAGT 20

What is claimed is:

1. A method for detecting the presence of a target single-stranded nucleic acid in a sample comprising the steps of:

(a) providing a nucleic acid probe comprising a single-stranded nucleic acid having a base sequence complementary to a base sequence of the target single-stranded nucleic acid;

(b) providing first and second reagents, both of which are capable of interacting with each other in the presence of a nucleic acid hybrid by charge transfer which occurs through stacks of base pairs forming a double helical structure of the nucleic acid hybrid;

(c) adding the nucleic acid probe to the sample to form a nucleic acid hybrid between the nucleic acid probe and the target single-stranded nucleic acid;

(d) adding the first reagent to the sample;

(e) adding the second reagent to the sample; and (f) detecting a change in the sample caused by the charge transfer between the first and second reagents, wherein the first and second reagents are different from each other, and wherein at least one of the first and second reagents is a pyrylium compound represented by the following formula I:

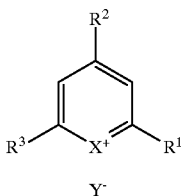

I wherein X is O, S, Se or Te, a first and second substituent selected from $R^1$, $R^2$, $R^3$, are independently substituted or unsubstituted aryl groups; the third substituent is a hydrogen atom, halogen atom, sulfonate group, amino group, styryl group, nitro group, hydroxyl group, carboxyl group, cyano group, substituted or unsubstituted lower alkyl group, substituted or unsubstituted cycloalkyl group, —A or —L—A, wherein L is II, III, IV, V, or VI as follows:

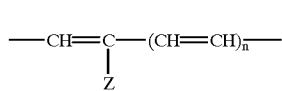

II wherein Z is a hydrogen atom or substituted or unsubstituted lower alkyl group and n is 0, 1, or 2,

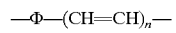

III wherein n is 0, 1 or 2, and Φ is substituted or unsubstituted o-, m-, or p-phenylene group,

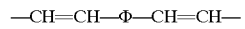

IV wherein Φ is substituted or unsubstituted o-, m-, or p-phenylene group,

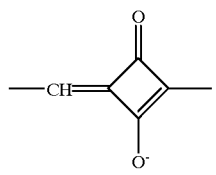

V

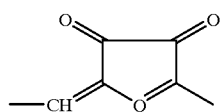

VI

A is a substituted or unsubstituted aryl group or —CH=$R^5$, wherein $R^5$ is a substituted or unsubstituted heterocyclic ring, a substituted or unsubstituted cycloalkyl group or a substituted or unsubstituted aromatic ring, and $Y^-$ is an anion.

2. The method according to claim 1, including conducting step (c) by adding the nucleic acid probe to the sample to form the hybrid, and then adding the first and second reagents to the sample containing the hybrid.

3. The method according to claim 1, including conducting step (c) by adding the nucleic acid to the sample containing the first reagent to form the hybrid in the presence of the first reagent and subsequently adding the second reagent to the sample.

4. The method according to claim 1, wherein the first reagent includes an electron donor and the second reagent includes an electron acceptor.

5. The method according to claim 4, wherein the electron acceptor is a substance which causes change in electron spin resonance spectrum on accepting an electron.

6. The method according to claim 1, wherein the step (d) comprises detecting an optically detectable change in the sample.

7. The method according to claim 6, wherein the step for detecting an optically detectable change in the sample comprises detecting an appearance of a novel absorption band.

8. The method according to claim 6, wherein the step for detecting an optically detectable change in the sample comprises detecting a change in absorption spectrum of the first reagent or the second reagent.

9. The method according to claim 1, wherein the step (d) comprises detecting a chemically detectable change in the sample.

10. The method according to claim 9, wherein the step of detecting a chemically detectable change in the sample comprises the steps of:

providing a third reagent capable of exhibiting detectable change when the third reagent reacts with the first reagent modified by the charge transfer or the second reagent modified by the charge transfer;

reacting the third reagent with the modified first reagent or the modified second reagent to cause the detectable change in the third reagent; and detecting the change in the third reagent.

11. The method according to claim 10, wherein the reaction between the third reagent and the modified first reagent or the modified second reagent is an antigen-antibody reaction.

12. The method according to claim 1, further comprising a step for irradiating light to the sample resulting from step (c).

13. The method according to claim 1, wherein the first and the second reagents are intercalators.

14. The method according to claim 13, wherein the first and the second reagents are each a pyrylium compound of the formula [I].

15. The method according to claim 1, wherein the change caused by the charge transfer between the reagents is irreversible.

16. A method for detecting the presence of a target single-stranded nucleic acid in a sample solution comprising the steps of:

(a) providing a probe comprising a single-stranded nucleic acid whose base sequence is complementary to that of the target single-stranded nucleic acid and having a first and a second reagent both of which are bound to the single-stranded nucleic acid of the probe, the first and second reagents being capable of interacting with each other when a hybrid is formed between the probe and the target single-stranded nucleic acid by charge transfer which occurs through stacks of base pairs forming a double helical structure of the hybrid;

(b) adding the probe to the sample solution to form a hybrid between the probe and the target single-stranded nucleic acid; and (c) detecting a change caused by the charge transfer between the first and second reagents in the sample, the change being detected when the target single-stranded nucleic acid is present in the sample solution, wherein the first and second reagents are different from each other, and wherein at least one of the first and second reagents is selected from a pyrylium compound represented by the following formula I:

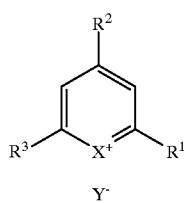

I wherein X is O, S, Se or Te, a first and second substituent selected from $R^1$, $R^2$, and $R^3$, are independently substituted or unsubstituted aryl groups; the third substituent is a hydrogen atom, halogen atom, sulfonate group, amino group, styryl group, nitro group, hydroxyl group, carboxyl group, cyano group, substituted or unsubstituted lower alkyl group, substituted or unsubstituted cycloalkyl group, —A or —L—A, wherein L is II, III, IV, V, or VI as follows:

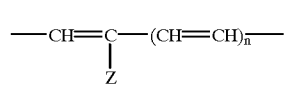

II wherein Z is a hydrogen atom or substituted or unsubstituted lower alkyl group and n is 0, 1, or 2,

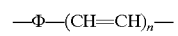

III wherein n is 0, 1 or 2, and Φ is substituted or unsubstituted o-, m-, or p-phenylene group,

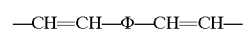

IV wherein Φ is substituted or unsubstituted o-, m-, or p-phenylene group,

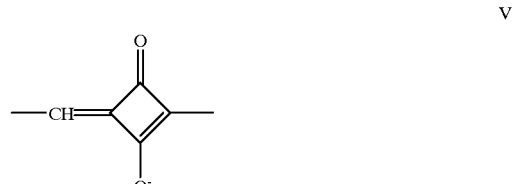

V

VI

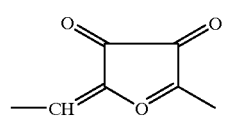

A is a substituted or unsubstituted aryl group or —CH=$R^5$, wherein $R^5$ is a substituted or unsubstituted heterocyclic ring, a substituted or unsubstituted cycloalkyl group or a substituted or unsubstituted aromatic ring, and $Y^-$ is an anion.

17. The method according to claim 16, wherein the step (c) comprises detecting an optically detectable change in the sample.

18. The method according to claim 17, wherein the step for detecting an optically detectable change in the sample comprises detecting an appearance of a novel absorption band.

19. The method according to claim 17, wherein the step for detecting an optically detectable change in the sample comprises detecting a change in absorption spectrum of the first reagent or the second reagent.

20. The method according to claim 16, wherein the step (c) comprises detecting a chemically detectable change in the sample.

21. The method according to claim 16, wherein the step for detecting a chemically detectable change in the sample comprises the steps of:

providing a third reagent capable of exhibiting detectable change when the third reagent reacts with the first reagent modified by the charge transfer or the second reagent modified by the charge transfer;

reacting the third reagent with the modified first reagent or the modified second reagent to cause the detectable change in the third reagent; and detecting the change in the third reagent.

22. The method according to claim 21, wherein the reaction between the third reagent and the modified first reagent or the modified second reagent is an antigen-antibody reaction.

23. The method according to claim 16, wherein the first reagent includes an electron donor and the second reagent includes an electron acceptor.

24. The method according to claim 23, wherein the electron acceptor is a substance which causes change in electron spin resonance spectrum on accepting an electron.

25. The method according to claim 16, wherein the change caused by the charge transfer between the first and second is irreversible.

26. The method according to claim 16, wherein the first reagent is a pyrylium compound of the formula [I] and the second reagent is a spin labelling agent selected from the group consisting of 4,4-dimethyloxazolidine-N-oxyl, 2,2,5,5-tetramethylpyrrolidine-N-oxyl, 2,2,6,6-tetramethylpiperidine-N-oxyl, riboflavin, N,N-dimethyl-2,7-diazapyrenium ion and derivatives thereof.

27. The method according to claim 16, wherein the first reagent is a pyrylium compound of the formula [I] and the second reagent is an intercalator selected from the group consisting of acridine, anthracene, pyrene, ethydium bromide, proflavin, porphyrin, thiazole orange dimer, oxazole yellow, 4,6-diamino-2-phenylindole dihydrochloride and propidium iodide.

28. The method according to claim 16, wherein the first reagent is a pyrylium compound of the formula [I] and the second reagent is selected from the group consisting of cyanine, azulene, dansyl, fluorescein, eosine, rhodamine and their derivatives.

29. The method according to claim 16, wherein the first and second reagents are each a pyrylium compound of the formula [I].

30. The method according to claim 29, wherein the pyrylium compound is selected from one of Compound Nos. 1–101 shown in Table 1 and 2.

31. A method for detecting the presence of a target single-stranded nucleic acid in a sample comprising the steps of:
(a) providing a probe comprising a single-stranded nucleic acid whose base sequence is complementary to that of the target single-stranded nucleic acid and a first reagent bound to the single-stranded nucleic acid of the probe;
(b) providing a second reagent capable of interacting with the first reagent when a hybrid is formed between the probe and the target single-stranded nucleic acid in the presence of the second reagent by a charge transfer which occurs through stacks of base pairs forming a double helical structure of the hybrid;
(c) adding the probe to the sample to form a hybrid between the probe and the target single-stranded nucleic acid;
(d) adding the second reagent to the sample; and
(e) detecting a change caused by the charge transfer between the first and second reagents, wherein the chance occurs when the target single-stranded nucleic acid is present in the sample,
wherein the first and second reagents are different from each other, and wherein at least one of the first and second reagents is selected from a pyrylium compound represented by the following formula I:

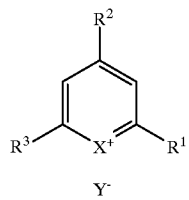

wherein X is O, S, Se or Te, a first and second substituent selected from $R^1$, $R^2$, and $R^3$, are independently substituted or unsubstituted aryl groups; the third substituent is a hydrogen atom, halogen atom, sulfonate group, amino group, styryl group, nitro group, hydroxyl group, carboxyl group, cyano group, substituted or unsubstituted lower alkyl group, substituted or unsubstituted cycloalkyl group, —A or —L—A, wherein L is II, III, IV, V, or VI as follows:

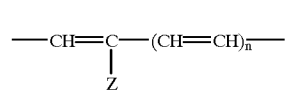

wherein Z is a hydrogen atom or substituted or unsubstituted lower alkyl group and n is 0, 1, or 2,

wherein n is 0, 1 or 2, and Φ is substituted or unsubstituted o-, m-, or p-phenylene group,

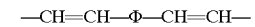

wherein Φ is substituted or unsubstituted o-, m-, or p-phenylene group,

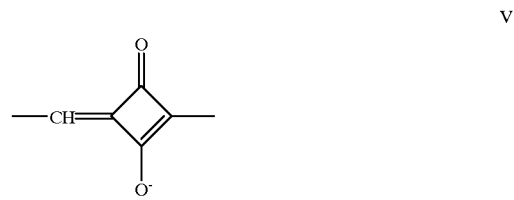

A is a substituted or unsubstituted aryl group or —CH═$R^5$, wherein $R^5$ is a substituted or unsubstituted heterocyclic ring, a substituted or unsubstituted cycloalkyl group or a substituted or unsubstituted aromatic ring, and $Y^-$ is an anion.

32. The method according to claim 31, wherein the first reagent includes an electron donor and the second reagent includes an electron acceptor.

33. The method according to claim 32, wherein the electron acceptor is a substance which causes change in electron spin resonance spectrum on accepting an electron.

34. The method according to claim 31, wherein the step (c) comprises detecting an optically detectable change in the sample.

35. The method according to claim 34, wherein the step for detecting an optically detectable change in the sample comprises detecting a spectrum change in ESR employing a spin-resonance.

36. The method according to claim 34, wherein the step for detecting an optically, detectable change in the sample comprises detecting an appearance of a novel absorption band.

37. The method according to claim 34, wherein the step for detecting an optically detectable change in the sample comprises detecting a change in absorption spectrum of the reagents.

38. The method according to claim 31, wherein the step (c) comprises detecting a chemically detectable change in the sample.

39. The method according to claim 38, wherein the step for detecting a chemically detectable change in the sample comprises:
  providing a third reagent capable of exhibiting detectable change when the third reagent reacts with the first reagent modified by the charge transfer or the second reagent modified by the charge transfer;
  reacting the third reagent with the modified first reagent or the modified second reagent to cause the detectable change in the third reagent; and
  detecting the change in the third reagent.

40. The method according to claim 39, wherein the reaction between the third reagent and the modified first reagent or the modified second reagent, is an antigen-antibody reaction.

41. The method according to claim 31, wherein the second reagent is an intercalator.

42. The method according to claim 31, wherein the first and second reagents are a pyrylium compound of the formula [I].

43. The method according to claim 31, further comprising a step for irradiating light to the sample resulting from step (b).

44. The method according to claim 31, wherein the change caused by the charge transfer is irreversible.

45. A probe for detecting a target single-stranded nucleic acid comprising: a single-stranded nucleic acid whose base sequence is complementary to that of the target single-stranded nucleic acid, a first reagent and a second reagent, the first and second reagents being bound to the nucleic acid of the probe, and being capable of interacting with each other when a hybrid is formed between the probe and the target single-stranded nucleic acid by charge transfer which occurs through stacks of base pairs forming a double helical structure of the hybrid, wherein the first and second reagents are different from each other, and wherein at least one of the first and second reagents is a pyrylium compound represented by the following formula I:

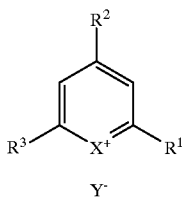

I wherein X is O, S, Se or Te, a first and second substituent selected from $R^1$, $R^2$, and $R^3$, are independently substituted or unsubstituted aryl groups; the third substituent is a hydrogen atom, halogen atom, sulfonate group, amino group, styryl group, nitro group, hydroxyl group, carboxyl group, cyano group, substituted or unsubstituted lower alkyl group, substituted or unsubstituted cycloalkyl group, —A or —L—A,
  wherein L is II, III, IV, V, or VI as follows:

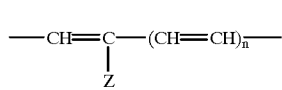

II wherein Z is a hydrogen atom or substituted or unsubstituted lower alkyl group and n is 0, 1, or 2,

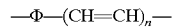

III wherein n is 0, 1 or 2, and Φ is substituted or unsubstituted o-, m-, or p-phenylene group,

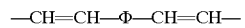

IV wherein Φ is substituted or unsubstituted o-, m-, or p-phenylene group,

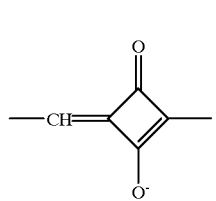

V

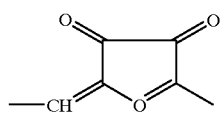

VI

A is a substituted or unsubstituted aryl group or —CH=$R^5$, wherein $R^5$ is a substituted or unsubstituted heterocyclic ring, a substituted or unsubstituted cycloalkyl group, or a substituted or unsubstituted aromatic ring, and $Y^-$ is an anion.

46. The probe according to claim 45, wherein the first reagent is an electron donor and the second reagent is an electron acceptor.

47. The probe according to claim 45, wherein both of the first and second reagents are intercalators which are incorporated into the double helical structure of the hybrid when hybridizing the probe with the target single-stranded nucleic acid.

48. The probe according to claim 45, wherein the charge transfer is initiated by light irradiation.

49. The probe according to claim 45, wherein the first reagent is bound to one terminal portion of the nucleic acid of the probe and the second reagent is bound to the other terminal portion of the nucleic acid of the probe.

50. The probe according the claim 45, wherein the first reagent is a pyrylium compound of the formula [I], and the second reagent is spin labeling agent selected from the group consisting of 4,4-dimethyloxazolidine, 2,2,5,5-tetramethylpyrrolidine-N-oxyl, 2,2,6,6-tetramethylpiperidine-N-oxyl, riboflavin, N,N-dimethyl-2,7-diazapyrenium ion and derivatives thereof.

51. The probe according to claim 45, wherein the first reagent is a pyrylium compound of the formula [I], and the second reagent is an intercalator selected from the group consisting of acridine, anthracene, pyrene, ethydium bromide, proflavin, porphyrin, thiazole orange dimer, oxazole yellow, 4-6-diamino-2-phenylindole dihydrochloride and propidium iodide.

52. The probe according to claim 45, wherein the first reagent is a pyrylium compound of the formula [I], and the second reagent is selected from the group consisting of cyanine, azulene, dansyl, fluorescein, eosine, rhodamine and their derivatives.

53. The probe according to claim 45, wherein both the first and second reagents are a pyrylium compound of formula [I].

54. The probe according to claim 53, wherein the pyrylium compound is selected from one of Compound Nos. 1–101 shown in Table 1 and 2.

55. A probe for detecting a target single-stranded nucleic acid comprising: a single-stranded nucleic acid whose base sequence is complementary to that of the target single-stranded nucleic acid, said single-stranded nucleic acid of the probe having an electron donor and an electron acceptor both of which are bound thereto, wherein a distance between the electron donor and the electron acceptor is from 50 to 80 Angstroms and wherein the electron donor and the electron acceptor are different compounds, and at least one of the electron donor and the electron acceptor is a pyrylium compound represented by the following formula I:

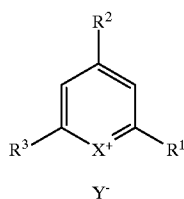

wherein X is O, S, Se or Te, a first and second substituent selected from $R^1$, $R^2$, and $R^3$, are independently substituted or unsubstituted aryl groups; the third substituent is a hydrogen atom, halogen atom, sulfonate group, amino group, styryl group, nitro group, hydroxyl group, carboxyl group, cyano group, substituted or unsubstituted lower alkyl group, substituted or unsubstituted cycloalkyl group, —A or —L—A, wherein L is II, III, IV, V, or VI as follows:

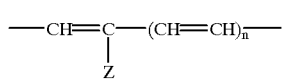

wherein Z is a hydrogen atom or substituted or unsubstituted lower alkyl group and n is 0, 1, or 2,

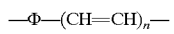

wherein n is 0, 1 or 2, and Φ is substituted or unsubstituted o-, m-, or p-phenylene group,

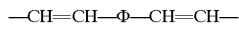

wherein Φ is substituted or unsubstituted o-, m-, or p-phenylene group,

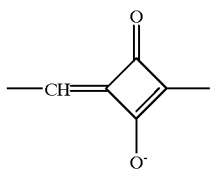

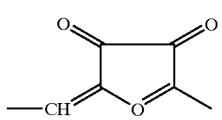

A is a substituted or unsubstituted aryl group or —CH=$R^5$, wherein $R^5$ is a substituted or unsubstituted heterocyclic ring, a substituted or unsubstituted cycloalkyl group or a substituted or unsubstituted aromatic ring, and $Y^-$ is an anion.

56. The probe according to claim 55, wherein the first reagent is a pyrylium compound of the formula [I], and the second reagent is spin labeling agent which is selected from the group consisting of 4,4-dimethyloxazolidine-N-oxyl, 2,2,5,5-tetramethylpyrrolidine-N-oxyl, riboflavin, N,N-dimethyl-2,7-diazapyrenium ion and derivatives thereof.

57. The probe according to claim 55, wherein the first reagent is a pyrylium compound of the formula [I], and the second reagent is an intercalator selected from the group consisting of acridine, anthracene, pyrene, ethydium bromide, proflavin, porphyrin, thiazole orange dimer, oxazole yellow, 4,6-diamino-2-phenylindole dihydrochloride and propidium iodide.

58. The probe according to claim 55, wherein both the first and second reagents are a pyrylium compound of formula [I].

59. The probe according to claim 58, wherein the pyrylium compound is selected from one of Compounds No. 1–101 shown in Table 1 and 2.

60. A process for determining if a hybrid in a sample is free from any mismatches, comprising the steps of:
(a) providing a sample containing a nucleic acid hybrid;
(b) adding 2-methyl-4,6-bis-(4-N,N-dimethylaminophenyl)pyrylium iodide and 4-methyl-2-6-diphenylpyrylium perchlorate to the sample;
(c) detecting a change caused by a charge transfer between the 2-methyl-4,6-bis-(4-N,N-dimethylaminophenyl)pyrylium and the 4-methyl-2,6-diphenyl pyrylium perchlorate which occurs through stacks of base pairs forming a double helical structure of the nucleic acid hybrid, the change being detected when the nucleic acid hybrid is free from any mismatches; and
(d) determining if the hybrid is free from any mismatches.

61. A process for determining if a nucleic acid hybrid in a sample is free from any mismatches, the nucleic acid hybrid containing a double helical structure formed between a probe and a target single-stranded nucleic acid in a sample comprising the steps of:
(a) providing a probe comprising a single-stranded nucleic acid having a base sequence complementary to that of the target single-stranded nucleic acid, and a first and a second reagent both of which are bound to the nucleic acid of the probe and capable of interacting with each other when a hybrid which is free from any mismatches is formed between the probe and the target single-stranded nucleic acid by charge transfer which occurs through stacks of base pairs forming a double helical structure of the hybrid;

(b) adding the probe to the sample to form a hybrid between the probe and the target single-stranded nucleic acid;
(c) detecting a change caused by the charge transfer between the first and second reagents, the change being detected when the target single-stranded nucleic acid is present in the sample; and
(d) determining if the hybrid resulting from the step (b) is free from any mismatches,
wherein the first and second reagents are different from each other, and wherein at least one of the first and second reagents is selected from a pyrylium compound represented by the following formula I:

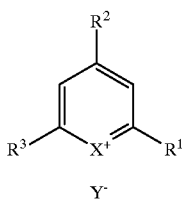

wherein X is O, S, Se or Te, a first and second substituent selected from $R^1$, $R^2$, and $R^3$, are independently substituted or unsubstituted aryl groups; the third substituent is a hydrogen atom, halogen atom, sulfonate group, amino group, styryl group, nitro group, hydroxyl group, carboxyl group, cyano group, substituted or unsubstituted lower alkyl group, substituted or unsubstituted cycloalkyl group, —A or —L—A,
wherein L is II, III, IV, V, or VI as follows:

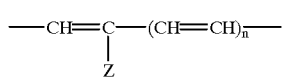

wherein Z is a hydrogen atom or substituted or unsubstituted lower alkyl group and n is 0, 1, or 2,

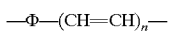

wherein n is 0, 1 or 2, and Φ is substituted or unsubstituted o-, m-, or p-phenylene group,

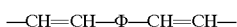

wherein Φ is substituted or unsubstituted o-, m-, or p-phenylene group,

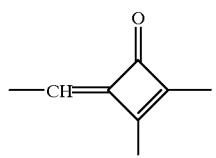

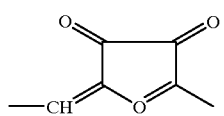

A is a substituted or unsubstituted aryl group or —CH=$R^5$, wherein $R^5$ is a substituted or unsubstituted heterocyclic ring, a substituted or unsubstituted cycloalkyl group or a substituted or unsubstituted aromatic ring, and $Y^-$ is an anion.

62. The process according to claim 61, wherein both of the first and the second reagents are a pyrylium compound of the formula [I].

63. The process according to any one of the claims 1, 16, 31, 55 and 61, wherein the pyrylium compound is represented by following formula:

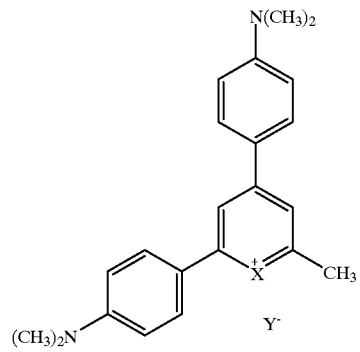

wherein X is O or S and $Y^-$ is an anion.

64. The process according to any one of claims 1, 16, 31, 55 and 61, wherein the pyrylium compound is represented by following formula:

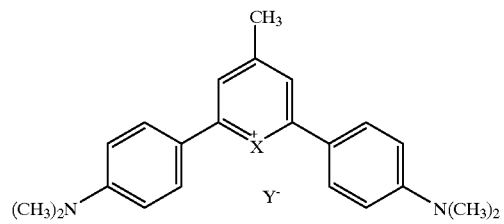

wherein X is O or S and $Y^-$ is an anion.

65. The probe according to any one of claims 51 or 52, wherein the pyrylium compound is represented by the following formula:

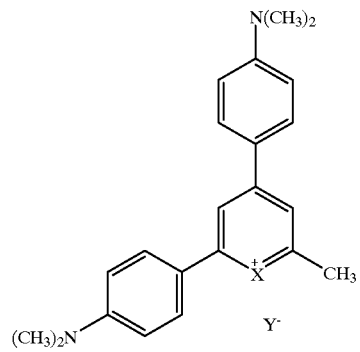

wherein X is O or S and $Y^-$ is an anion.

66. The probe according to claim 58, wherein one of the pyrylium compounds is represented by the following formula:

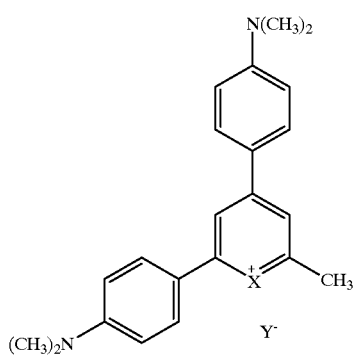
wherein X is O or S and Y⁻ is an anion.
67. The probe according to claim 55, wherein the other pyrylium compound is represented by the following formula:
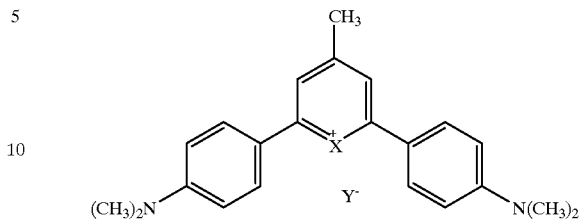
wherein X is O or S and Y⁻ is an anion.
* * * * *

UNITED STATES PATENT AND TRADEMARK OFFICE
CERTIFICATE OF CORRECTION

PATENT NO. : 6,156,506
DATED : December 5, 2000
INVENTOR(S) : Nobuko Yamamoto et al.

It is certified that error appears in the above-identified patent and that said Letters Patent is hereby corrected as shown below:

<u>Title page, Item [57] ABSTRACT,</u>
Line 4, "therebetween" should read -- therebetween, --.

<u>Column 7,</u>
Line 3, "a re" should read -- are --; and
Line 8, "on e" should read -- one --.

<u>Column 10,</u>
Line 32, "be" should be deleted;
Line 50, "be also" should read -- also be --;
Line 54, "paris" should read -- pairs --;
Line 56, "be also" should read -- also be --.

<u>Column 19,</u>
Table 1, Compound 16, "R=H" should read -- $R_7$=H --;

Table 1, Compound 19, " 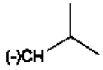 " should read --  --;

Table 1, Compound 20, " 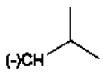 " should read --  --.

<u>Column 21,</u>
Table 1, Compound 21, " 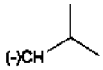 " should read --  --;

Table 1, Compound 22, " 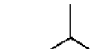 " should read --  --;

Table 1, Compound 23, " 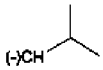 " should read --  --;

Table 1, Compound 24, "  " should read --  --.

<u>Column 23,</u>
Table 1, Compound 27, " 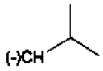 " should read --  --;

Table 1, Compound 28, "  " should read --  --;

Table 1, Compound 29, "  " should read --  --.

UNITED STATES PATENT AND TRADEMARK OFFICE
CERTIFICATE OF CORRECTION

PATENT NO. : 6,156,506
DATED : December 5, 2000
INVENTOR(S) : Nobuko Yamamoto et al.

It is certified that error appears in the above-identified patent and that said Letters Patent is hereby corrected as shown below:

Column 25,
Table 1, Compound 48, "$R_8=\phi\text{-}_{N(CH3)2}$" should read -- $R_8=\phi\text{-}N(CH_3)_2$ --.

Column 31,
Compound 33, "  " should read -- --.

Column 36,
Compound 44, "  " should read -- --.

Signed and Sealed this

Seventeenth Day of May, 2005

JON W. DUDAS
*Director of the United States Patent and Trademark Office*